(12) United States Patent
Tajima et al.

(10) Patent No.: US 9,074,239 B2
(45) Date of Patent: Jul. 7, 2015

(54) FLAVIN-BINDING GLUCOSE DEHYDROGENASE, METHOD FOR PRODUCING FLAVIN-BINDING GLUCOSE DEHYDROGENASE, AND GLUCOSE MEASUREMENT METHOD

(75) Inventors: Ryoko Tajima, Noda (JP); Kozo Hirokawa, Noda (JP); Eriko Yoshihara, Noda (JP); Yasuko Tanabe, Noda (JP)

(73) Assignee: KIKKOMAN CORPORATION, Noda-shi, Chiba (JP)

( * ) Notice: Subject to any disclaimer, the term of this patent is extended or adjusted under 35 U.S.C. 154(b) by 0 days.

(21) Appl. No.: 14/124,559

(22) PCT Filed: Jun. 6, 2012

(86) PCT No.: PCT/JP2012/064523
§ 371 (c)(1),
(2), (4) Date: Dec. 6, 2013

(87) PCT Pub. No.: WO2012/169512
PCT Pub. Date: Dec. 13, 2012

(65) Prior Publication Data
US 2014/0287445 A1 Sep. 25, 2014

(30) Foreign Application Priority Data
Jun. 7, 2011 (JP) ................... 2011-126893

(51) Int. Cl.
| | |
|---|---|
| C12N 9/04 | (2006.01) |
| C12Q 1/54 | (2006.01) |
| C12Q 1/00 | (2006.01) |
| C12Q 1/32 | (2006.01) |

(52) U.S. Cl.
CPC ........ *C12Q 1/54* (2013.01); *C12Q 1/006* (2013.01); *C12Q 1/32* (2013.01); *G01N 2333/904* (2013.01); *C12N 9/0006* (2013.01); *C12Y 101/9901* (2013.01)

(58) Field of Classification Search
None
See application file for complete search history.

(56) References Cited

U.S. PATENT DOCUMENTS

| 7,741,100 B2 | 6/2010 | Kitabayashi et al. |
|---|---|---|
| 8,445,246 B2 | 5/2013 | Tajima et al. |
| 2006/0063217 A1 | 3/2006 | Omura et al. |
| 2008/0003628 A1 | 1/2008 | Kitabayashi et al. |
| 2008/0090278 A1 | 4/2008 | Kitabayashi et al. |
| 2009/0176262 A1 | 7/2009 | Omura et al. |
| 2009/0181408 A1 | 7/2009 | Tanaka et al. |
| 2009/0317848 A1 | 12/2009 | Kawaminami et al. |
| 2010/0297743 A1 | 11/2010 | Omura et al. |
| 2010/0323378 A1 | 12/2010 | Honda et al. |
| 2011/0045513 A1 | 2/2011 | Takenaka et al. |
| 2011/0053194 A1 | 3/2011 | Yuuki et al. |
| 2013/0309750 A1 | 11/2013 | Tajima et al. |
| 2014/0057331 A1 | 2/2014 | Tajima et al. |

FOREIGN PATENT DOCUMENTS

| EP | 1862543 A1 | 12/2007 |
|---|---|---|
| EP | 2241621 A1 | 10/2010 |
| EP | 2508600 A | 10/2010 |
| JP | 2005176602 A | 7/2005 |
| JP | 2007-289148 A | 11/2007 |
| JP | 2008-154574 A | 7/2008 |
| JP | 2008-237210 A | 10/2008 |
| JP | 2010-035448 A | 2/2010 |
| JP | 4494978 B2 | 6/2010 |
| JP | 2010-269056 A | 12/2010 |
| JP | 4648993 B2 | 3/2011 |
| JP | 2011-115156 A | 6/2011 |
| WO | 2004/058958 A1 | 7/2004 |
| WO | WO 2006/101239 A1 | 9/2006 |
| WO | WO 2007/139013 A1 | 12/2007 |
| WO | WO 2009/069381 A1 | 6/2009 |
| WO | WO 2009/084616 A1 | 7/2009 |
| WO | WO 2010/140431 A1 | 12/2010 |
| WO | WO 2011/004654 A1 | 1/2011 |
| WO | WO 2011/068050 A1 | 6/2011 |

OTHER PUBLICATIONS

Yamaoka et al., Site Directed Mutagenesis Studies of FAD-dependent Glucose Dehydrogenase Catalytic Subunit of Burkholderia Cepacia, Biotechnol. Lett., Nov. 2008 30(11), pp. 1967-1972.
U.S. Appl. No. 14/355,326, filed Apr. 30, 2014.
International Preliminary Report on Patentability and Written Opinion for PCT/JP2012/064523 mailed Dec. 27, 2013.
International Search Report dated Sep. 4, 2012 for PCT/JP2012/064523.
U.S. Appl. No. 13/991,087, filed May 31, 2013, First Named Inventor: Ryoko Tajima.
*Pharmaceutical and Medical Devices Safety Information*, No. 206, Oct. 2004, Pharmaceutical and Food Safety Bureau, Ministry of Health, Labour and Welfare (in English).

(Continued)

*Primary Examiner* — Suzanne M Noakes
(74) *Attorney, Agent, or Firm* — Holtz, Holtz, Goodman & Chick PC

(57) ABSTRACT

A flavin-binding glucose dehydrogenase (FAD-GDH), which in addition to having high substrate specificity and adequate desirable heat stability, is suitable for efficient production, preferably using *E. coli*, yeast or molds and the like as host cells. The FAD-GDH has amino acid substitutions at positions equivalent to one or more locations selected from the group consisting of position 213, position 368 and position 526 in the amino acid sequence described in SEQ ID NO: 8. The FAD-GDH is acquired from a culture by inserting a gene encoding the FAD-GDH into host cells such as *E. coli*. A preferable example of the FAD-GDH is FAD-GDH, in which a signal peptide region present in an N-terminal region has been deleted from the amino acid sequence of Mucor-derived FAD-GDH, and which has the aforementioned amino acid substitutions. The FAD-GDH can be preferably used in clinical diagnosis.

18 Claims, 1 Drawing Sheet

(56) References Cited

OTHER PUBLICATIONS

T.C. Bak et al., "Studies on the glucose dehydrogenase of *Aspergillus oryzae*: I. Induction of its synthesis by p-benzoquinone and hydroquinone", *Biochim. Biophys. Acta*, 139, 265-276 (1967) (in English).

T.C. Bak et al., "Studies on the glucose dehydrogenase of *Aspergillus oryzae*: II. Purification and physical and chemical properties", *Biochim. Biophys. Acta*, 139, 277-293 (1967) (in English).

T.C. Bak et al., "Studies on the glucose dehydrogenase of *Aspergillus oryzae*: III. General enzymatic properties", *Biochim. Biophys. Acta*, 146, 317-327 (1967) (in English).

T.C. Bak et al., "Studies on the glucose dehydrogenase of *Aspergillus oryzae*: IV. Histidyl residue as an active site", *Biochim. Biophys. Acta*, 146, 328-335 (1967) (in English).

Extended European Search Report dated Dec. 22, 2014, issued in counterpart European Application No. 12797050.7.

Glucose dehydrogenase [Flavin] (2005, updated) http://www.uniprot.org/uniprot/P18172, pp. 1-9.

SEQ-Align (2015) pp. 1-2.

SEQ-Align III (2015) pp. 1-2.

SEQ-Align II (2015) pp. 1-2.

Krasney, et al., "Evolution of the Glucose Dehydrogenase Gene in Drosophila", *Mol. Biol. Evol.*, vol. 7, pp. 155-177.

FIG. 1

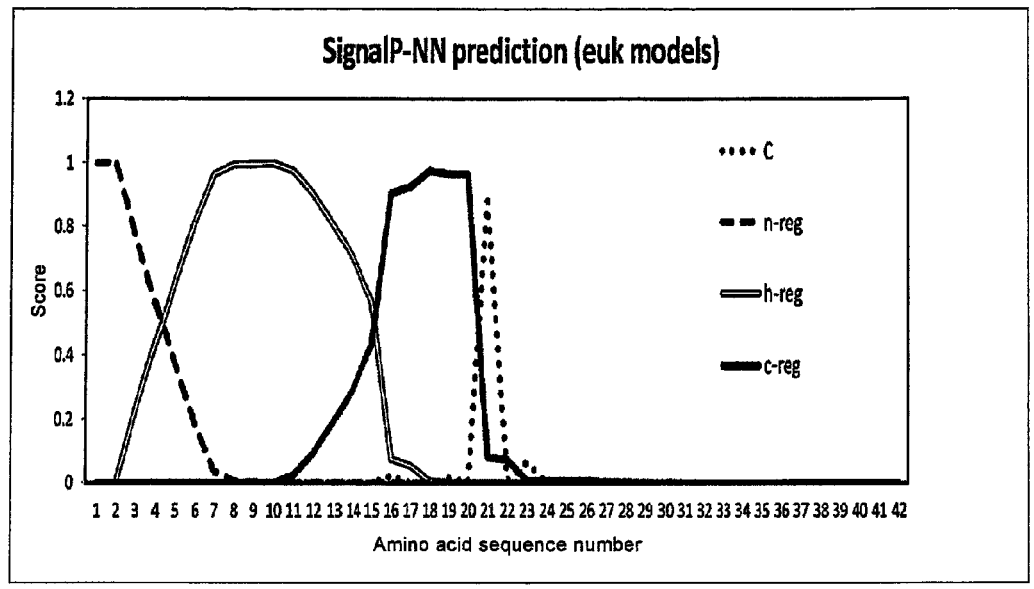

```
>Sequence           length = 42
# Measure  Position  Value  Cutoff  signal peptide?
    max. C    21      0.761  0.32   YES
    max. Y    21      0.734  0.33   YES
    max. S     7      0.967  0.87   YES
    mean S    1-20    0.805  0.48   YES
         D    1-20    0.769  0.43   YES
# Most likely cleavage site between pos. 20 and 21: ASA-QQ
```

FIG. 2

```
MpFull   MKITAAIITVATAFASFASAQQDTNSSSTDTYDYVIVGGGVAGLALASRISENKDVTVAV   60
MpNS1    -------------------MQQDTNSSSTDTYDYVIVGGGVAGLALASRISENKDVTVAV
MpNS2    -------------------MQDTNSSSTDTYDYVIVGGGVAGLALASRISENKDVTVAV
```

MpFull : N-terminal region of full-length GDH containing signal peptide
MpNS1: N-terminal region of GDH in which starting codon M has been added to the amino acid on the N-terminal by cleaving a signal peptide
MpNS2: N-terminal region of GDH in which the amino acid on the N-terminal has been changed to starting codon M by cleaving a signal peptide

FLAVIN-BINDING GLUCOSE DEHYDROGENASE, METHOD FOR PRODUCING FLAVIN-BINDING GLUCOSE DEHYDROGENASE, AND GLUCOSE MEASUREMENT METHOD

CROSS-REFERENCE TO RELATED APPLICATION

This application is a U.S. national phase application of International Application PCT/JP2012/064523, filed Jun. 6, 2012.

TECHNICAL FIELD

The present invention relates to a flavin-binding glucose dehydrogenase having high substrate specificity and superior heat stability, a method for producing flavin-binding glucose dehydrogenase, and a glucose measurement method using thereof.

BACKGROUND ART

Blood glucose concentration (blood sugar level) is an important marker for diabetes. Devices for self-monitoring of blood glucose (SMBG) using electrochemical biosensors are widely used by diabetes patients as a device for monitoring their own blood sugar levels. The biosensors used in SMBG devices have conventionally used an enzyme such as glucose oxidase (GOD) that uses glucose as a substrate. However, since GOD has the characteristic of using oxygen as an electron acceptor, SMBG devices using GOD have the potential for preventing the obtaining of accurate measured values due to dissolved oxygen in the measurement sample having an effect on measured values.

On the other hand, various types of glucose dehydrogenases (GDH) are known as enzymes that also use glucose as a substrate but do not use oxygen as an electron acceptor. More specifically, a type of GDH that uses nicotinamide adenine dinucleotide (NAD) or nicotinamide adenine dinucleotide phosphate (NADP) as coenzyme (NAD(P)-GDH) and a type of GDH that uses pyrroloquinoline quinone (PQQ) as coenzyme (PQQ-GDH) have been discovered, and these enzymes are used in the biosensors of SMBG devices. However, NAD (P)-GDH lacks enzyme stability while also having the problem of requiring addition of a coenzyme, while PQQ-GDH has low substrate specificity, causing it to act on sugar compounds other than glucose such as maltose, D-galactose or D-xylose, thereby allowing sugar compounds in measurement samples other than glucose to have an effect on measured values, and resulting in the problem of being unable to obtain accurate measured values.

Recently, PQQ-GDH has been reported to act on maltose contained in transfusion solutions when SMBG devices using PQQ-GDH as a biosensor are used by diabetes patients to measure blood sugar levels, causing measured values to be higher than actual blood sugar levels, and occurrences of disorders such as hypoglycemia caused by treatment based on those values have been reported. In addition, similar occurrences have been determined to also be possible in patients undergoing galactose tolerance tests and xylose absorption tests (see, for example, Non-Patent Document 1). In response to this, when the Pharmaceutical and Food Safety Bureau of the Ministry of Health, Labour and Welfare conducted a cross-reactivity study for the purpose of investigating effects on measured blood sugar levels in the case of having added various sugars to a glucose solution, in the case of adding maltose at 600 mg/dL, D-galactose at 300 mg/dL or D-xylose at 200 mg/dL, measured values obtained with a blood glucose monitoring kit using the PQQ-GDH method were indicated to be nearly 2.5 to 3 times higher than actual glucose concentration. Namely, measured values were determined to be made inaccurate by maltose, D-galactose and D-xylose present in measurement samples, thus resulting in a fervent desire to develop GDH having high substrate specificity enabling specific measurement of glucose without being affected by sugar compounds causing measurement error in this manner.

With the foregoing in view, attention came to be focused on types of GDH that use coenzymes other than those previously described. For example, although details relating to substrate specificity are not described, GDH has been reported that is derived from *Aspergillus oryzae* (see, for example, Non-Patent Documents 2 to 5). In addition, glucose dehydrogenase derived from genera *Aspergillus* and *Penicillium* that uses flavin adenine dinucleotide (FAD) as a coenzyme (FAD-GDH) has been disclosed (see, for example, Patent Documents 1 to 3), while FAD-GDH derived from *Aspergillus* species has been disclosed that has reduced action on D-xylose (see, for example, Patent Document 4).

However, although the aforementioned enzymes demonstrate the property of having low reactivity with respect to one or more types of sugar compounds that are not D-glucose, they do not have the property of having sufficiently low reactivity with respect to any of maltose, D-galactose and D-xylose. In contrast, the applicant found that flavin-binding GDHs isolated from the genus *Mucor* have the superior property of demonstrating sufficiently low reactivity with respect to maltose, D-galactose and D-xylose (see, for example, Patent Document 5). In addition, the use of this GDH was confirmed to enable accurate measurement of glucose concentration without being affected by maltose, D-galactose or D-xylose even under conditions in which these sugar compounds are present (see, for example, Patent Document 5). This superior substrate specificity is a major characteristic indicating the superiority of these *Mucor*-derived FAD-GDHs in terms of practical use. Moreover, the applicant disclosed the gene sequence and amino acid sequence of one of these *Mucor*-derived FAD-GDHs in Patent Document 5, and also provided a disclosure of recombinant expression using *E. coli* and *Aspergillus sojae* as host that produces this *Mucor*-derived FAD-GDH.

On the other hand, methods for large-volume production of useful enzymes that use microorganisms such as *E. coli* as hosts are widely known, and in cases in which it is difficult to produce a sufficient amount of enzyme in the original source microorganisms, there are many examples in which the use of such methods enables enzymes to be produced efficiently. With this same intention, the applicant also attempted recombinant production using *E. coli* based on gene sequence information of *Mucor*-derived FAD-GDH. However, when *Mucor*-derived FAD-GDH gene is attempted to be expressed in *E. coli*, in addition to the expression level being extremely low, the heat stability was determined to decrease considerably in comparison with FAD-GDH inherently produced by source microorganisms, and this was thought to be due to the absence of the addition of sugar chains due to differences in the host. Therefore, the inventors of the present invention found that FAD-GDH, in which an amino acid sequence equivalent to the signal peptide region present in the N-terminal region of the amino acid sequence of *Mucor*-derived FAD-GDH, and more specifically, an N-terminal region containing an amino acid sequence equivalent to MKITAAIIT-VATAFASFASA, has been deleted, is capable of more efficiently producing FAD-GDH in *E. coli* in comparison with the case of using the full-length *Mucor*-derived FAD-GDH gene in which the N-terminal region has not been deleted. However, this FAD-GDH missing the N-terminal region was still considered to be inadequate with respect to heat stability.

Furthermore, the applicant separately found in Patent Document 6 that *Mucor*-derived FAD-GDH expressed in yeast belonging to the genus *Zygosaccharomyces* has superior substrate specificity and heat resistance. Namely, in the case of, for example, having expressed *Mucor*-derived FAD-GDH gene not missing the N-terminal region in yeast, the expressed *Mucor*-derived FAD-GDH was found to have superior heat resistance in comparison with the case of expressing *Mucor*-derived FAD-GDH gene missing the N-terminal region in *E. coli*. However, since heat treatment is likely to be carried out during the fabrication of sensor chips, when considering the potential for being subjected to severe heat conditions accompanying such applications, it was necessary to continue to attempt to impart even greater heat resistance even with respect to *Mucor*-derived FAD-GDH expressed in yeast.

PRIOR ART DOCUMENTS

Patent Documents

[Patent Document 1] Japanese Unexamined Patent Publication No. 2007-289148
[Patent Document 2] Japanese Patent No. 4494978
[Patent Document 3] International Publication No. WO 07/139,013
[Patent Document 4] Japanese Unexamined Patent Publication No. 2008-237210
[Patent Document 5] Japanese Patent No. 4648993
[Patent Document 6] Japanese Patent Application No. 2010-269056

Non-Patent Documents

[Non-Patent Document 1] Pharmaceuticals and Medical Devices Safety Information No. 206, October 2004, Pharmaceutical and Food Safety Bureau, Ministry of Health, Labour and Welfare.
[Non-Patent Document 2] Studies on the glucose dehydrogenase of *Aspergillus oryzae*: I. Induction of its synthesis by p-benzoquinone and hydroquinone, T. C. Bak and R. Sato, Biochim. Biophys. Acta, 139, 265-276 (1967).
[Non-Patent Document 3] Studies on the glucose dehydrogenase of *Aspergillus oryzae*: II. Purification and physical and chemical properties, T. C. Bak, Biochim. Biophys. Acta, 139, 277-293 (1967).
[Non-Patent Document 4] Studies on the glucose dehydrogenase of *Aspergillus oryzae*: III. General enzymatic properties, T. C. Bak, Biochim. Biophys. Acta, 146, 317-327 (1967).
[Non-Patent Document 5] Studies on the glucose dehydrogenase of *Aspergillus oryzae*: IV. Histidyl residue as an active site, T. C. Bak and R. Sato, Biochim. Biophys. Acta, 146, 328-335 (1967).

DISCLOSURE OF THE INVENTION

Problems to be Solved by the Invention

A problem of the present invention is to provide an FAD-GDH, which in addition to having high substrate specificity and adequate heat stability, is suitable for efficient production preferably using *E. coli*, yeast or molds and the like as host cells.

Means for Solving the Problems

As a result of conducting extensive studies to solve the aforementioned problems and searching for FAD-GDH, which in addition to having high substrate specificity and adequate heat stability, is suitable for efficient production by preferably using *E. coli*, yeast or molds and the like as host cells, the inventors of the present invention found that FAD-GDH having high substrate specificity and adequate heat stability can be obtained by introducing a mutation into known FAD-GDH. Moreover, the inventors of the present invention found that FAD-GDH having this mutation and missing a specific site of the N-terminal is a novel FAD-GDH that is superior from the viewpoint of allowing efficient production using *E. coli* and the like as host cells. Moreover, the inventors of the present invention found that the effects of the aforementioned mutation are effective even in the case of producing full-length FAD-GDH from which the signal peptide has not been removed using molds or yeast as hosts, thereby leading to completion of the present invention.

Namely, the present invention relates to that described below.

[1] A flavin-binding glucose dehydrogenase consisting of the amino acid sequence indicated in SEQ ID NO: 8, an amino acid sequence having sequence identity with that amino acid sequence of 90% or more, or an amino acid sequence in which one or several amino acids in that amino acid sequence have been deleted, substituted or added; and, characterized by having one or more amino acid substitutions selected from the group consisting of:
  valine at position 213 in the amino acid sequence described in SEQ ID NO: 8 or an amino acid residue equivalent thereto,
  threonine at position 368 in the amino acid sequence described in SEQ ID NO: 8 or an amino acid residue equivalent thereto, and
  isoleucine at position 526 in the amino acid sequence described in SEQ ID NO: 8 or an amino acid residue equivalent thereto.

[2] The flavin-binding glucose dehydrogenase described in [1], characterized by having one or more amino acid substitutions selected from the group consisting of:
  valine at position 232 in the amino acid sequence described in SEQ ID NO: 1,
  threonine at position 387 in the amino acid sequence described in SEQ ID NO: 1, and
  isoleucine at position 545 in the amino acid sequence described in SEQ ID NO: 1.

[3] A flavin-binding glucose dehydrogenase consisting of the amino acid sequence indicated in SEQ ID NO: 8, an amino acid sequence having sequence identity with that amino acid sequence of 90% or more, or an amino acid sequence in which one or several amino acids in that amino acid sequence have been deleted, substituted or added; and, characterized by having one or more amino acid substitutions at positions corresponding to amino acids selected from the group consisting of:
  the amino acid residue at a position equivalent to position 213 in the amino acid sequence described in SEQ ID NO: 8 is alanine, methionine, cysteine, glutamine or glutamic acid,
  the amino acid residue at a position equivalent to position 368 in the amino acid sequence described in SEQ ID NO: 8 is alanine, valine, glycine, serine or cysteine, and the amino acid residue at a position equivalent to position 526 in the amino acid sequence described in SEQ ID NO: 8 is valine, threonine, serine, proline, alanine, tyrosine, lysine, histidine, phenylalanine or glutamic acid.

[4] The flavin-binding glucose dehydrogenase described in [3], characterized by having one or more amino acid substitutions at positions corresponding to amino acids selected from the group consisting of:

the amino acid residue at a position equivalent to position 232 in the amino acid sequence described in SEQ ID NO: 1 is alanine, methionine, cysteine, glutamine or glutamic acid, the amino acid residue at a position equivalent to position 387 in the amino acid sequence described in SEQ ID NO: 1 is alanine, valine, glycine, serine or cysteine, and the amino acid residue at a position equivalent to position 545 in the amino acid sequence described in SEQ ID NO: 1 is valine, threonine, serine, proline, alanine, tyrosine, lysine, histidine, phenylalanine or glutamic acid.

[5] A flavin-binding glucose dehydrogenase consisting of an amino acid sequence in which an amino acid region portion equivalent to a signal peptide region present in the N-terminal region has been deleted from the amino acid sequence of wild-type flavin-binding glucose dehydrogenase derived from a microorganism classified in the subphylum Mucoromycotina, preferably the class Mucoromycetes, more preferably the order Mucorales, even more preferably the family Mucoraceae, and most preferably the genus *Mucor*, an amino acid sequence having sequence identity with the aforementioned amino acid sequence of 90% or more, or an amino acid sequence in which one or several amino acids in the aforementioned amino acid sequence have been deleted, substituted or added; and, providing with the following during recombinant production in *E. coli*:

action: exhibits glucose dehydrogenase activity in the presence of an electron acceptor, molecular weight: molecular weight of the polypeptide chain of the protein is about 70 kDa, and substrate specificity: has lower reactivity to maltose, D-galactose and D-xylose with respect to reactivity to D-glucose; wherein, during recombinant production in *E. coli*, has residual activity of 3% or more after subjecting to heat treatment for 10 minutes at 35° C.

[6] A flavin-binding glucose dehydrogenase gene encoding the flavin-binding glucose dehydrogenase described in any of [1] to [5].

[7] A flavin-binding glucose dehydrogenase gene consisting of:

DNA encoding the amino acid sequence indicated in SEQ ID NO: 8,

DNA consisting of the base sequence indicated in SEQ ID NO: 9,

DNA encoding the amino acid sequence indicated in SEQ ID NO: 10, or

DNA having a base sequence having sequence homology with the base sequence indicated in SEQ ID NO: 9 of 90% or more and encoding a protein having flavin-binding glucose dehydrogenase enzyme activity.

[8] A vector containing the flavin-binding glucose dehydrogenase gene described in [6] or [7].

[9] A host cell containing the vector described in [8].

[10] A method for producing flavin-binding glucose dehydrogenase, comprising the following steps:

a step for culturing the host cells described in [9], a step for expressing flavin-binding glucose dehydrogenase gene contained in the host cells, and a step for recovering flavin-binding glucose dehydrogenase from the culture.

[11] A method for measuring glucose using the flavin-binding glucose dehydrogenase described in [1] to [5].

[12] A glucose assay kit characterized by containing the flavin-binding glucose dehydrogenase described in [1] to [5].

[13] A glucose sensor characterized by containing the flavin-binding glucose dehydrogenase described in [1] to [5].

Effects of the Invention

According to the present invention, FAD-GDH can be provided, which in addition to having high substrate specificity and adequate heat stability, is suitable for efficient production preferably using *E. coli*, yeast or molds and the like as host cells.

BRIEF DESCRIPTION OF THE DRAWINGS

FIG. 1 is a graph showing predicted signal peptide cleavage sites in *Mucor*-derived FAD-GDH as an example of an enzyme able to serve as an origin of the FAD-GDH of the present invention.

FIG. 2 indicates amino acid sequences of N-terminal portions in *Mucor*-derived FAD-GDH as an example of an enzyme able to serve as an origin of the FAD-GDH of the present invention and in an example of an N-terminal-deficient mutant thereof.

BEST MODE FOR CARRYING OUT THE INVENTION (Principle of Action of FAD-GDH of Present Invention and Method for Measuring Activity)

The FAD-GDH of the present invention catalyzes a reaction that forms glucono-δ-lactone by oxidizing a hydroxyl group of glucose in the presence of an electron acceptor in the same manner as known wild-type or mutant FAD-GDH.

Activity of the FAD-GDH of the present invention can be measured with the measuring system indicated below using, for example, phenazine methosulfate (PMS) and 2,6-dichloroindophenol (DCIP) as electron acceptors:

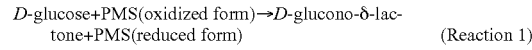
(Reaction 1)

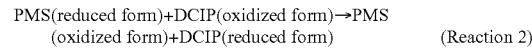
(Reaction 2)

More specifically, in Reaction 1, PMS (reduced form) is first formed accompanying oxidation of D-glucose. DCIP is then reduced accompanying oxidation of PMS (reduced form) as the subsequent Reaction 2 proceeds. The degree of consumption of this DCIP (reduced form) can be detected as a change in the amount of absorbance at a wavelength of 600 nm, and enzyme activity can be determined based on this change.

More specifically, the activity of flavin-binding GDH can be measured in accordance with the following procedure. 2.05 mL of 50 mM phosphate buffer (pH 6.5), 0.6 mL of 1 M D-glucose solution and 0.15 mL of 2 mM DCIP solution are mixed followed by warming for 5 minutes at 37° C. Next, 0.1 mL of 15 mM PMS solution and 0.1 mL of enzyme sample solution are added to initiate the reaction. Absorbance is measured at the start of the reaction and over time, and the amount of the decrease in absorbance at 600 nm per minute (ΔA600) as the enzyme reaction proceeds is determined followed by calculating flavin-binding GDH activity in accordance with the following equation. At this time, 1 U of flavin-binding GDH activity is defined as the amount of enzyme that reduces 1 μmol of DCIP in 1 minute in the presence of D-glucose at a concentration of 200 mM at 37° C.

$$\text{GDH activity (U/ml)} = \frac{-(\Delta A600 - \Delta A600_{blank}) \times 3.0 \times df}{16.3 \times 0.1 \times 1.0} \quad \text{[Equation 1]}$$

Furthermore, the value of 3.0 in the equation represents the liquid volume (mL) of the reaction reagents and enzyme sample, the value of 16.3 represents the millimolar molecular extinction coefficient ($cm^2/\mu mol$) under the activity measurement conditions, the value of 0.1 represents the liquid volume (mL) of the enzyme solution, the value of 1.0 represents the cell path length (cm), $\Delta 600_{blank}$ represents the reduction in absorbance at 600 nm per minute in the case of initiating the reaction by adding 10 mM acetate buffer (pH 5.0) instead of enzyme sample solution, and df represents the dilution factor.

(Amino Acid Sequence of FAD-GDH of Present Invention)

The FAD-GDH of the present invention is consisting of the amino acid sequence indicated in SEQ ID NO: 8, an amino acid sequence having high sequence identity with that amino acid sequence, such as that having sequence identity of preferably 80% or more, more preferably 85% or more, even more preferably 90% or more, and most preferably 95% or more, or an amino acid sequence in which one or several amino acids in that amino acid sequence have been deleted, substituted or added, and has one or more amino acid substitutions at positions corresponding to amino acids selected from the location equivalent to position 213, the location equivalent to position 368, and the location equivalent to 526 in the amino acid sequence described in SEQ ID NO: 8.

Preferably, the amino acid substitution at the aforementioned location equivalent to position 213 refers to a substitution in which the amino acid at the aforementioned location equivalent to position 213 is substituted with any of alanine, methionine, cysteine, glutamine or glutamic acid, the amino acid substitution at the location equivalent to position 368 refers to a substitution in which the amino acid at the aforementioned location equivalent to position 368 is substituted with any of alanine, valine, glycine, serine or cysteine, and the amino acid substitution at the location equivalent to position 526 refers to a substitution in which the amino acid at the aforementioned location equivalent to position 526 is substituted with any of valine, threonine, serine, proline, alanine, tyrosine, lysine, histidine, phenylalanine or glutamic acid. Furthermore, in SEQ ID NO: 8, the unsubstituted amino acid at position 213 of the present invention is valine, that at position 368 is threonine, and that at position 526 is isoleucine.

Although various types of variations are presumed to exist in the FAD-GDH of the present invention within the range of the aforementioned sequence identity, all of these can be included in the FAD-GDH of the present invention provided the enzymological properties of these various types of FAD-GDH are similar to those of the FAD-GDH of the present invention described in the present description. FAD-GDH having such amino acid sequences is industrially useful as FAD-GDH, which in addition to having high substrate specificity and adequate heat stability, is suitable for efficient production using *E. coli*, yeast or molds and the like as host cells.

In addition, in the FAD-GDH of the present invention, it is important that the amino acid at the aforementioned location equivalent to position 213 be any of alanine, methionine, cysteine, glutamine or glutamic acid, that the amino acid at the location equivalent to position 368 be any of alanine, valine, glycine, serine or cysteine, and that the amino acid at the location equivalent to position 526 be any of valine, threonine, serine, proline, alanine, tyrosine, lysine or histidine, while it is not important as to whether or not they are the result of an unnatural substitution procedure. For example, in the case of introducing a desired substitution using as a starting material a protein in which amino acids at the aforementioned locations inherently differ from the desired residues of the present invention by using a known technology therein in the manner of the protein described by SEQ ID NO: 8, those desired amino acid residues can be introduced by substitution. On the other hand, in the case of acquiring a desired protein by a known peptide total synthesis method, or in the case of synthesizing an entire gene sequence so as to encode a protein having a desired amino acid sequence and then acquiring the desired protein on the basis thereof, or in the case of inherently having a sequence that is found in nature, the FAD-GDH of the present invention can be obtained without having to go through a step of unnatural substitution.

(Examples of Naturally-Occurring FAD-GDH Serving as Source of FAD-GDH of Present Invention)

The FAD-GDH of the present invention can be acquired by using a known protein as a starting material and modifying that protein. In particular, the use of a starting material having numerous similarities with the enzymological properties desired in the FAD-GDH of the present invention is advantageous in terms of acquiring a desired FAD-GDH.

Examples of the aforementioned starting material include known FAD-GDH. Preferable examples of microorganisms derived from known FAD-GDH include microorganisms classified in the subphylum Mucoromycotina, preferably the class Mucoromycetes, more preferably the order Mucorales and even more preferably the family Mucoraceae. Specific examples of preferable starting materials for acquiring the FAD-GDH of the present invention include FAD-GDH derived from the genus *Mucor*, the genus *Absidia* or the genus *Actinomucor*.

Specific examples of preferable microorganisms classified in the genus *Mucor* include *Mucor prainii*, *Mucor javanicus*, *Mucor dimorphosphorus* and *Mucor circinelloides* f. *circinelloides*. More specifically, these include *Mucor prainii* NISL0103, *Mucor javanicus* NISL0111 and *Mucor circinelloides* f. *circinelloides* NISL0117. Specific examples of preferable microorganisms belonging to the genus *Absidia* include *Absidia cylindrospora* and *Absidia hyalospora*. More specifically, these include *Absidia cylindrospora* NISL0211 and *Absidia hyalospora* NISL0218. A specific example of preferable microorganism classified in the genus *Actinomucor* is *Actinomucor elegans*. More specifically, this includes *Actinomucor elegans* NISL9082. Furthermore, the aforementioned microbial strains are deposited with the Noda Institute for Scientific Research (NISL), and cultures can be obtained by going through the prescribed procedures.

(Substrate Specificity of FAD-GDH of Present Invention)

The FAD-GDH of the present invention is characterized by having high substrate specificity. More specifically, the FAD-GDH of the present invention is characterized by having extremely low reactivity with respect to maltose, D-galactose or D-xylose in the same manner as the *Mucor*-derived FAD-GDH described in Japanese Patent No. 4648993 previously discovered by the inventors of the present invention. More specifically, reactivity with respect to maltose, D-galactose or D-xylose is 2% or less in each case when based on a value of 100% for reactivity with respect to D-glucose. Since the FAD-GDH used in the present invention has high substrate specificity in this manner, it is capable of accurately measuring the amount of D-glucose even in samples from patients receiving administration of a transfusion solution containing maltose or samples from patients undergoing galactose tolerance tests or xylose tolerance tests without being affected by sugar compounds such as maltose, D-galactose or D-xylose contained in measurement samples.

In addition, the FAD-GDH of the present invention is also characterized by demonstrating extremely low measured values during measurements using sugar compounds such as maltose, D-galactose or D-xylose as substrates instead of D-glucose as previously described, while also enabling accurate measurement of glucose measured values even under conditions in which there is contamination by sugar compounds such as maltose, D-galactose or D-xylose. More specifically, measured values in the case one or more contaminating sugar compounds selected from maltose, D-galactose or D-xylose are present are 96% to 103%, while measured values in the case three types of contaminating sugar compounds consisting of maltose, D-galactose or D-xylose are present are 96% to 104%, based on a value of 100% for the reactivity with respect to D-glucose under conditions in which these contaminating sugar compounds are not present. In the case of using FAD-GDH having such characteristics, glucose levels can be accurately measured even under circumstances in which maltose, D-galactose or D-xylose are present in a measurement sample.

Various enzymological properties can be investigated using known techniques for specifying various properties of enzymes, such as by using methods described in the following examples. Various properties of enzymes can also be investigated to a certain degree in a liquid culture of a microorganism that produces flavin-binding GDH used in the present invention or at an intermediate stage of the purification process, and more specifically, can be investigated using purified enzyme.

(Deletion of N-Terminal Amino Acid Region when Obtaining FAD-GDH of Present Invention by Modifying *Mucor*-Derived FAD-GDH)

In the case of obtaining the FAD-GDH of the present invention by modifying the aforementioned *Mucor*-derived FAD-GDH, and particularly when producing the FAD-GDH of the present invention in a host such as *E. coli*, by deleting a fixed region of the amino acid region present in an N-terminal region from the amino acid sequence of the starting substance in the form of *Mucor*-derived FAD-GDH, and more specifically, a portion of the amino acid region equivalent to a signal peptide region, the effect is obtained of being able to improve the expression level thereof in the case of expressing in *E. coli*. Predicting the signal peptide is an effective means for examining this deleted region of the N-terminal. The signal peptide can be predicted to a certain degree by using a suitable tool, and in actuality, a preferable deleted region can be determined by verifying the region based on this information. A known example of such a signal peptide prediction tool is the web-based signal peptide prediction program Signal P (www.cbs.dtu.dk/services/SignalP-2.0/).

A preferable example of an N-terminal amino acid deleted region when obtaining the FAD-GDH of the present invention by modifying *Mucor*-derived FAD-GDH is an N-terminal region containing a region equivalent to a signal peptide present in the N-terminal region of *Mucor*-derived FAD-GDH. More specifically, when using as an example the *Mucor*-derived FAD-GDH having the amino acid sequence described in SEQ ID NO: 1, the expression level and/or production level of the FAD-GDH of the present invention produced by an *E. coli* transformant can be increased by deleting a DNA region encoding an N-terminal region containing the amino acid sequence MKITAAIITVATAFASFASA indicated in SEQ ID NO: 19 present in the N-terminal thereof. This region (up to the 20th amino acid from the N-terminal) is suggested to have the possibility of being a signal peptide as indicated in FIG. 1.

Furthermore, the aforementioned specific amino acid sequence and the number of amino acid residues deleted are not intended to be limiting, but rather are able to include variations having a fixed range as defined in the present invention. Namely, "an amino acid sequence equivalent to MKITAAIITVATAFASFASA (SEQ ID NO: 19) present in the N-terminal thereof" refers to an amino acid sequence having a fixed sequence identity with FAD-GDH having the amino acid sequence described in SEQ ID NO: 1 (for example, 85% or more, preferably 90% or more, and more preferably 95% or more). Correspondence of "an equivalent location and/or sequence" between FAD-GDH having amino acid sequence identity equal to or greater than that indicated above can be easily determined by comparing the amino acid sequences of various types of FAD-GDH with the amino acid sequence of the FAD-GDH of SEQ ID NO: 1 using existing amino acid identity analytical software such as Genetyx-Mac (Software Development).

Other FAD-GDH having high sequence identity with the *Mucor*-derived FAD-GDH discovered by the inventors of the present invention have currently not been reported. However, since there is typically a high possibility of enzyme proteins having mutually high sequence identity having similar protein structures in regions of high identity, there are numerous known examples of being able to impart similar effects with respect to enzyme properties by analyzing the correspondence of amino acid sequences of a plurality of enzymes having a fixed level or more of amino acid sequence identity by analyzing the identity thereof, and introducing similar mutations or deletions and the like into the locations of other amino acids or amino acid sequences equivalent to the location of a specific amino acid or an amino acid sequence region of one of those enzymes. Thus, with respect to FAD-GDH as well, attempts can easily be made to similarly delete an amino acid sequence of an equivalent region in other FAD-GDH as a strategy for obtaining similar effects with respect to these FAD-GDH by utilizing the findings of the present invention relating to the deleted region of an N-terminal peptide of the FAD-GDH in the present invention exemplified by SEQ ID NO: 1.

In addition, the deleted region of the N-terminal peptide of the FAD-GDH in the present invention is not necessarily only a signal peptide region. For example, in addition to deleting only a signal peptide region, a region adjacent to the signal peptide region that includes a region within a range that does not have a detrimental effect on enzyme activity can also be deleted in addition to the signal peptide region per se. More specifically, as shown in FIG. 2, for example, MKITAAIITVATAFASFASA (SEQ ID NO: 19) present in the N-terminal may be deleted from the N-terminal sequence (indicated by MpSN1 in the drawing, SEQ ID NO: 8) of full-length *Mucor*-derived FAD-GDH (indicated by MpFull in the drawing, SEQ ID NO: 1), or the amino acid sequence MKITAAIITVATAFASAFASAQ (SEQ ID NO: 20), of a form in which one additional residue has been further deleted, may be deleted (indicated by NpNS2 in the drawing, SEQ ID NO: 10). Additional amino acids may also be deleted provided the deletions are within a range that does not have a detrimental effect on enzymological properties of the resulting enzyme. For example, the amino acid sequence MKITAAIITVATAFASFASAQQDTNSS (sequence extending to the 27th amino acid, not shown in the drawings, SEQ ID NO: 21)

present in the N-terminal may be deleted, or the amino acid sequence MKITAAIITVATAFASFASAQQDTNSSS (sequence extending to the 28th amino acid, not shown in the drawings, SEQ ID NO: 22), of a form in which one additional residue has been further deleted, may be deleted. What is important in the present invention is that the N-terminal signal peptide region be substantially deleted, and whether or not a small region is also deleted in addition to the N-terminal signal peptide region is not a necessary condition of the present invention, and provided similar effects are demonstrated, a plurality of variations of N-terminal region deletion are included in the FAD-GDH of the present invention. In addition, depending on the source or host of the FAD-GDH, even in the case of deleting a slightly shorter N-terminal region from a region thought to be the N-terminal signal peptide region, such as in the case of deleting an N-terminal region that is one to a plurality of residues shorter, in the case there are no substantial differences observed between the effect of this deletion and the effect of having deleted the entire region thought to be the N-terminal signal peptide region, or between the effect when having deleted a longer N-terminal region, including the entire region thought to be the N-terminal signal peptide region, variations of the present invention can be included.

Although there are no limitations on the method used to delete an N-terminal peptide, a known means can be used, and an example of which consists of changing the amino acid on the N-terminal to a starting codon in the form of methionine and expressing by signal peptide cleavage. Alternatively, FAD-GDH deficient in signal peptide can also be expressed in *E. coli* by adding a starting codon in the form of methionine to the amino acid on the N-terminal by signal peptide cleavage. Other possible methods consist of predicting deletion of a peptide containing a small adjacent region containing the signal peptide as previously described, changing the amino acid on the N-terminal to a starting codon in the form of methionine and expressing in the case of having carried out cleavage at the predicted region, and adding a starting codon in the form of methionine to the amino acid on the N-terminal by cleavage.

When cleaving a fixed N-terminal region, although the amino acid sequence of the resulting FAD-GDH differs by one residue depending on whether the newly formed N-terminal is substituted with methionine or methionine is added without substituting, this procedure is carried out in order to normalize protein expression from a gene by imparting a starting codon in the case the N-terminal newly formed by deletion of the signal peptide is no longer methionine, and is not a necessary condition of the present invention.

Whether or not the expression level of the target enzyme has increased in comparison with the state in which a signal peptide sequence is present can be confirmed by comparing total activity levels per milliliter of liquid culture before and after introducing a mutation into the sequence. Furthermore, deletion of the signal peptide can be confirmed by confirming with the N-terminal amino acid sequence using Edman degradation. PSORT and SignalP are frequently used as signal peptide prediction programs. These programs can be accessed on the web at psort.nibb.ac.jp/ and www.cbs.dtu.dk/services/SignalP-2.0/, respectively.

Since addition of a sugar chain does not occur in the case of having deletion of the N-terminal as previously described and being expressed in *E. coli*, the molecular weight of the FAD-GDH of the present invention is less than that of wild-type *Mucor*-derived FAD-GDH. In the case of calculating from the amino acid sequence or measuring by SDS-polyacrylamide electrophoresis, the molecular weight of the polypeptide chain portion of the FAD-GDH protein of the present invention is about 70 kDa.

Furthermore, in the case of producing the FAD-GDH of the present invention in a host such as yeast or mold, FAD-GDH can be expressed without deleting the signal peptide region. In such cases, the expressed FAD-GDH can have a full-length sequence or a sequence approximating full length. In this type of FAD-GDH as well, the effect of substituting an amino acid at a position equivalent to the location of an amino acid substitution specified in the present invention is the same. Namely, the present invention includes mutants similar to FAD-GDH in which the N-terminal signal peptide has not been deleted.

(Improvement of Heat Resistance in FAD-GDH of Present Invention)

When the mutant FAD-GDH of the present invention is expressed in *E. coli*, residual activity after subjecting to heat treatment for 10 minutes at 35° C. under the reaction conditions described in the activity measurement method and heat stability test method described in the present description is 3% or more, preferably 20% or more, more preferably 30% or more, even more preferably 40% or more, still more preferably 50% or more, even more preferably 60% or more, even more preferably 70% or more, and most preferably 80% or more. This high level of heat resistance cannot be possessed by FAD-GDH obtained by expressing in *E. coli* FAD-GDH gene not having a specific amino acid residue at the prescribed location that contributes to the prescribed improvement of heat resistance as defined in the FAD-GDH of the present invention (to be referred to as "wild-type FAD-GDH" in the present invention), and as a result thereof, FAD-GDH having improved heat resistance can be produced in a host such as *E. coli*. Examples of plasmids containing a gene that encodes this FAD-GDH of the present invention include pET-22b-MpNS1, pET-22b-MpNS1-M2, pET-22b-MpNS1-M3, pET-22b-MpNS1-M4, pET-22b-MpNS1-M5, pET-22b-MpNS1-M6, pET-22b-MpNS1-M7, pET-22b-MpNS1-M8, pET-22b-MpNS1-M9, pET-22b-MpNS1-M10, pET-22b-MpNS1-M11, pET-22b-MpNS1-M12, pET-22b-MpNS1-M13, pET-22b-MpNS1-M14, pET-22b-MpNS1-M15, pET-22b-MpNS1-M16, pET-22b-MpNS1-M17, pET-22b-MpNS1-M18, pET-22b-MpNS1-M19, pET-22b-MpNS1-M20, pET-22b-MpNS1-M21, pET-22b-MpNS1-M22 and pET-22b-MpNS1-M23. In addition, an example of a host microorganism that produces the FAD-GDH of the present invention is *E. coli* strain BL21(DE3)/pET-22b-MpNS1.

As was previously described, FAD-GDH of the present invention having high substrate specificity and superior heat stability can be obtained by, for example, first acquiring a gene encoding an amino acid sequence that approximates the amino acid sequence of SEQ ID NO: 8 using an arbitrary method, and then introducing an amino acid substitution at any of the locations equivalent to prescribed locations in SEQ ID NO: 8.

A "location equivalent to the amino acid sequence of SEQ ID NO: 8" referred to here, for example, refers to the same location in an alignment in the case of having aligned the amino acid sequence of SEQ ID NO: 8 with another amino acid sequence of FAD-GDH having sequence identity with SEQ ID NO: 8 (preferably of 80% or more, more preferably of 85% or more, even more preferably of 90% or more, and most preferably of 95% or more). Furthermore, sequence identity of an amino acid sequence can be calculated by a program such as the maximum matching or search homology program of Genetyx-Mac (Software Development) or by a program such as the maximum matching or multiple alignment program of DNASIS Pro (Hitachi Software).

In addition, an example of a method for specifying the "same location in an alignment" can be carried out by comparing amino acid sequences using a known algorithm such as the Lipman-Pearson algorithm, and imparting maximum identity to retained amino acid residues present in the amino acid sequence of FAD-GDH. By aligning the amino acid sequences of various types of FAD-GDH using this type of method, the same locations of homologous amino acid residues in each FAD-GDH sequence can be determined irrespective of insertions or deletions in the amino acid sequence. Since the same locations in an alignment are thought to be present at the same locations in a three-dimensional structure, they can be assumed to have similar effects with respect to heat stability performance of a target FAD-GDH.

An example of the FAD-GDH of the present invention is FAD-GDH having an amino acid substitution at a position equivalent to at least one of position 213, position 368 and position 526 in the amino acid sequence of SEQ ID NO: 8. Moreover, an example of the FAD-GDH of the present invention is a modified FAD-GDH in which, in the amino acid sequence of SEQ ID NO: 8, the amino acid substitution is selected from the group consisting of V213A, V213M, V213C, V213Q, V213E, T368A, T368V, T368G, T368S, T368C, I526V, I526T, I526S, I526P, I526A, I526Y, I526K, I526H, I526F and I526E.

Here, "V213A", for example, means that V (Val) at position 213 is substituted with A (Ala). In addition, "T368A" means that T (Thr) at position 368 is substituted with A (Ala). Moreover, "I526V" means that I (Ile) at position 526 is substituted with V (Val).

Furthermore, in the present invention, the "location equivalent to valine at position 213 of the amino acid sequence described in SEQ ID NO: 8" refers to an amino acid at the same location as valine at position 213 of the FAD-GDH of SEQ ID NO: 8 in the case of having compared the alignment of a determined amino acid sequence of FAD-GDH with the alignment of the amino acid sequence of Mucor-derived FAD-GDH indicated in SEQ ID NO: 8. As a result, an amino acid sequence can be aligned and specified by a method for specifying the aforementioned "same position in an alignment".

In addition, the "location equivalent to threonine at position 368 of the amino acid sequence described in SEQ ID NO: 8" refers to an amino acid at the same location as threonine at position 368 of the FAD-GDH of SEQ ID NO: 8 in the case of having compared the alignment of a determined amino acid sequence of FAD-GDH with the alignment of the amino acid sequence of Mucor-derived FAD-GDH indicated in SEQ ID NO: 8. This can also be specified by aligning amino acid sequences using the method described above.

Moreover, the "location equivalent to isoleucine at position 526 of the amino acid sequence described in SEQ ID NO: 8" refers to an amino acid at the same location as isoleucine at position 526 of the FAD-GDH of SEQ ID NO: 8 in the case of having compared the alignment of a determined amino acid sequence of FAD-GDH with the alignment of the amino acid sequence of Mucor-derived FAD-GDH indicated in SEQ ID NO: 8. This can also be specified by aligning amino acid sequences using the method described above.

For example, in SEQ ID NO: 1, which is an example of the full-length amino acid sequence of Mucor-derived FAD-GDH, the "location equivalent to valine at position 213 of the amino acid sequence of SEQ ID NO: 8" refers to valine at position 232 of the amino acid sequence described in SEQ ID NO: 1. In addition, in SEQ ID NO: 1, the "location equivalent to threonine at position 232 of the amino acid sequence described in SEQ ID NO: 8" refers to threonine at position 387 of the amino acid sequence described in SEQ ID NO: 1. Moreover, in SEQ ID NO: 1, the "location equivalent to isoleucine at position 526 of the amino acid sequence described in SEQ ID NO: 8" refers to isoleucine at position 545 of the amino acid sequence described in SEQ ID NO: 1. In this manner, since an "equivalent location" can be specified in an amino acid sequence differing from SEQ ID NO: 8 by using the amino acid sequence described in SEQ ID NO: 8 as a reference and aligning the amino acid sequence using a method for specifying "the same location in an alignment", whether an "equivalent location" in an amino acid sequence differing from SEQ ID NO: 8 is actually equivalent to the nth amino acid in that differing amino acid sequence can be easily confirmed. Mutants having a mutation at an equivalent location in a sequence having identity with SEQ ID NO: 8 or SEQ ID NO: 9 in this manner are also included in the scope of the present invention.

(Acquisition of Gene Encoding FAD-GDH of Present Invention)

A genetic engineering technique is preferably used to efficiently acquire the FAD-GDH of the present invention. A commonly used gene cloning method is used to acquire FAD-GDH gene encoding the FAD-GDH of the present invention (hereinafter to be referred to as FAD-GDH gene). For example, in order to acquire the FAD-GDH of the present invention by using a known FAD-GDH as a starting material and modifying that known FAD-GDH, chromosomal DNA or mRNA can be extracted according to an ordinary method such as the method described in Current Protocols in Molecular Biology (Wiley Interscience, 1989) from known microbial cells or various other cells having the ability to produce FAD-GDH. Moreover, cDNA can also be synthesized using mRNA as a template. A chromosomal DNA or cDNA library can be prepared by using chromosomal DNA or cDNA obtained in this manner.

Next, suitable probe DNA is synthesized based on amino acid sequence information of known FAD-GDH and this is used to select FAD-GDH gene having high substrate specificity from a chromosomal DNA or cDNA library, or DNA containing a target gene fragment encoding FAD-GDH having high substrate specificity is amplified by a suitable polymerase chain reaction (PCR) method such as 5'-RACE or 3'-RACE by preparing suitable primer DNA based on the aforementioned amino acid sequence, after which these DNA fragments are coupled to allow the obtaining of DNA containing the full length of the target FAD-GDH gene.

These FAD-GDH genes having high substrate specificity are preferably coupled to (inserted in) various types of vectors in consideration of handling ease. For example, DNA encoding FAD-GDH gene can be acquired by using a chemical such as Qiagen (Qiagen) from recombinant plasmids such as pET-22b-MpFull, pET-22b-MpNS1 or pET-22b-MpNS2 containing DNA encoding Mucor-derived FAD-GDH gene.

The vector of the present invention is not limited to the aforementioned plasmids, and any arbitrary vector known among persons with ordinary skill in the art can be used, examples of which include a bacteriophage and cosmid. Preferable specific examples include pET-22b(+), pET-16b (Novagen), pUC-18 and pBluescriptII SK+ (Stratagene).

A method consisting of introducing a mutation into a gene encoding a starting material in the form of FAD-GDH, and selecting the FAD-GDH of the present invention having high substrate specificity and superior heat stability by using the enzymological properties of the FAD-GDH expressed from various types of mutant genes can be employed as a method for acquiring the FAD-GDH of the present invention having high substrate specificity and superior heat stability by using a known FAD-GDH as a starting material.

Mutagenic treatment of the FAD-GDH gene used as a starting substance can be carried out by a known arbitrary method corresponding to the intended form of the mutation. Namely, a wide variety of methods can be used, including methods that allow a mutagenic chemical to contact and act on FAD-GDH gene or recombinant DNA incorporating that gene, ultraviolet irradiation methods, genetic engineering techniques and methods utilizing protein engineering techniques.

Examples of mutagenic chemicals used in the aforementioned mutagenic treatment include hydroxylamine, N-methyl-N'-nitro-N-nitrosoguanine, nitrous acid, sulfurous acid, hydrazine, formic acid and 5-bromouracil.

The various conditions under which contact and action are allowed to occur can be determined corresponding to the type of chemical used, and there are no particular limitations thereon provided they are capable of actually inducing a desired mutation in *Mucor*-derived FAD-GDH gene. Normally, a desired mutation can be induced by allowing a mutagenic chemical to contact and act for 10 minutes or more, and preferably for 10 minutes to 180 minutes, at a reaction temperature of 20° C. to 80° C. and at a chemical concentration of preferably 0.5 M to 12 M. In the case of carrying out ultraviolet irradiation as well, irradiation can be carried out in accordance with ordinary methods as previously described (Chemistry Today, p. 24-30, June 1989).

A technique known as site-specific mutagenesis can typically be used as a method that utilizes protein engineering techniques. Examples thereof include the Kramer method (Nucleic Acids Res., 12, 9441 (1984); Methods Enzymol., 154, 350 (1987); Gene 37, 73 (1985)), the Eckstein method (Nucleic Acids Res., 13, 8749 (1985); Nucleic Acids Res., 13, 8765 (1985); Nucleic Acids Res., 14, 9679 (1986)), and the Kunkel method (Proc. Natl. Acad. Sci. U.S.A., 82, 488 (1985); Methods Enzymol., 154, 367 (1987)). Specific examples of methods for transforming base sequences present in DNA include methods using commercially available kits (such as the Transformer Mutagenesis Kit (Clontech), the EXOIII/Mung Bean Deletion Kit (Stratagene), and the Quick Change Site-Directed Mutagenesis Kit (Stratagene).

In addition, a commonly used technique known as the polymerase chain reaction method can also be used (Technique, 1, 11 (1989)).

Furthermore, in addition to the aforementioned gene modification methods, a desired modified FAD-GDH gene having superior heat stability and high substrate specificity can be synthesized directly by organic synthesis methods or enzymatic synthesis methods.

In the case of determining or confirming the DNA base sequence of the FAD-GDH gene of the present invention after having been selected according to any of the arbitrary methods described above, a system such as the CEQ2000 Multi Capillary DNA Analysis System (Beckman Coulter) may be used.

(Vector and Host Cells Inserted with FAD-GDH of Present Invention)

The FAD-GDH gene of the present invention obtained in the manner described above can be incorporated into a vector such as a bacteriophage, cosmid or plasmid used in the transformation of prokaryotic or eukaryotic cells followed by transformation or transduction of host cells corresponding to each vector in accordance with ordinary methods.

Examples of prokaryotic host cells that can be used include microorganisms belonging to the genus *Escherichia*, such as *E. coli* strain K-12, *E. coli* strain BL21(DE3), *E. coli* strain JM109, *E. coli* strain DH5α, *E. coli* strain W3110 or *E. coli* strain C600 (all of which are available from TakaraBio), and host cells inserted with DNA (transformants) can be obtained by transforming or transducing these host cells. An example of a method that can be used to introduce a recombinant vector into host cells consists of introducing recombinant DNA in the presence of calcium ions in the case the host cells are microorganisms belonging to the species *E. coli*. Moreover, electroporation may also be used. Commercially available competent cells (such as ECOS Competent *Escherichia coli* BL21(DE), Nippon Gene) may also be used.

In addition, an example of eukaryotic cells is yeast. Examples of microorganisms classified as yeast include *Zygosaccharomyces* species, *Saccharomyces* species, *Pichia* species and *Candida* species. The inserted gene may also contain a marker gene for enabling selection of transformed cells. Examples of marker genes include genes such as URA3 or TRP1 that complement the nutrient requirements of the host. In addition, the inserted gene preferably contains a promoter or other control sequence capable of expressing the gene of the present invention in host cells (such as a secretion signal sequence, enhancer sequence, terminator sequence or polyadenylation sequence). Specific examples of promoters include GAL1 promoter and ADH1 promoter. Although known methods such as methods using lithium acetate (Methods Mol. Cell. Biol., 5, 255-269 (1995)) or electroporation (J. Microbiol. Methods, 55 (2003), 481-484) can be preferably used to transform yeast, the method used is not limited thereto, but rather transformation may also be carried out by various arbitrary methods such as the spheroblast method or glass bead method.

In addition, other examples of eukaryotic host cells include mold cells such as *Aspergillus* species or *Trichoderma* species. The inserted gene preferably contains a promoter (such as a tef1 promoter) or other control sequence (such as a secretion signal sequence, enhancer sequence, terminator sequence or polyadenylation sequence) capable of expressing the gene of the present invention in host cells. In addition, the inserted gene may also contain a marker gene such as niaD or pyrG for enabling selection of transformed cells. The inserted gene may also contain a homologous recombination region for insertion into an arbitrary chromosome site. A known method such as a method using polyethylene glycol and calcium chloride following the formation of protoplasts (Mol. Gen. Genet., 218, 99-104 (1989)) can be preferably used to transform filamentous fungi.

(Selection of Host Cells Producing FAD-GDH of Present Invention)

A method like that described below, for example, may be used to efficiently select strains producing the FAD-GDH of the present invention. First, several replicas of the resulting host cells (transformants) are removed from LB agar medium on which they have formed colonies to fresh agar medium such as sterile velveteen cloth and cultured in that medium. When the colonies on the agar medium to which the replicas have been transferred have reached sufficient size, a film immersed in a bacteriolytic agent such as lysozyme is layered over the medium followed by allowing to stand undisturbed for 1 hour at room temperature to lyse the cells. At this time, the lysed crude enzyme liquid is adsorbed into the film.

Next, the aforementioned film into which crude enzyme liquid has adsorbed is allowed to stand undisturbed for 1 minute to 1 hour at 35° C. followed by layering with a film immersed in a reaction liquid having a composition that results in the generation of color if FAD-GDH acts (10 mM acetate buffer (pH 5.0) containing glucose, PMS and DCIP) and observing the degree of purple color formed. Although the degree of coloring by the colonies is low in the case of wild-type FAD-GDH not having heat resistance, the degree of coloring by the colonies increases in the case of the FAD-GDH of the present invention that has acquired heat resistance. Utilizing this coloring makes it possible to select transformants that produce FAD-GDH having improved heat resistance by comparing with the degree of coloring of strains producing wild-type FAD-GDH.

Alternatively, the following method may also be used to efficiently select strains producing the FAD-GDH of the present invention. First, host cells having plasmids that have undergone mutagenic treatment (transformants) are inoculated into TY medium (1% Bacto Tryptone, 0.5% Bacto Yeast Extract, 0.5% NaCl (pH 7.0)) containing 100 μg/mL of ampicillin and 1 mM IPTG followed by shake culturing overnight at 25° C. Following completion of culturing, cells gathered by centrifuging for 5 minutes at 9,000 rpm are suspended in 10 mM acetate buffer (pH 5.0) and subjected to ultrasonic treatment to obtain a cell extract containing modified FAD-GDH. Next, the resulting cell suspension is diluted with enzyme diluent (10 mM acetate buffer (pH 5.0)) to prepare an enzyme liquid having a concentration of about 0.5 U/ml (0.2 ml, two aliquots). One of the two aliquots is stored at 4° C., while the other is subjected to heat treatment for 10 minutes at 35° C., and the FAD-GDH activity of each sample is measured following treatment. The residual activity (%) of each sample is calculated by comparing the level of activity after treating for 10 minutes at 35° C. based on a value of 100 for the enzyme activity of the cell suspension stored at 4° C., and transformants that produce FAD-GDH having improved heat resistance can be obtained by selecting those strains in which residual activity (%) has improved in comparison with wild-type FAD-GDH that has not undergone mutagenic treatment. More severe conditions may be set for the heat treatment temperature for calculating residual activity (%) as is required for mutant selection.

Modified FAD-GDH having even more superior heat stability as well as transformants having other production abilities can also be obtained by repeatedly subjecting FAD-GDH genes having superior heat stability determined in this manner to further mutation.

(Production of FAD-GDH of Present Invention)

The FAD-GDH of the present invention may be produced by culturing host cells that produce the FAD-GDH of the present invention acquired in the manner described above, expressing flavin-binding glucose dehydrogenase gene contained in the aforementioned host cells, and then isolating the flavin-binding glucose dehydrogenase from the aforementioned culture.

Examples of media used to culture the aforementioned host cells include media obtained by adding one or more types of inorganic salts such as sodium chloride, monopotassium phosphate, dipotassium phosphate, magnesium sulfate, magnesium chloride, ferric chloride, ferric sulfate or manganese sulfate to one or more types of nitrogen sources such as yeast extract, tryptone, peptone, beef extract, corn stiplica or soy bean or wheat bran percolate, followed by suitably adding a sugar source or vitamins and the like as necessary.

Although there no limitations on the pH of the media, it can be adjusted to, for example, pH 6 to pH 9.

Culturing is carried out for 4 hours to 24 hours at a culture temperature of 10° C. to 42° C. and preferably a temperature of about 25° C., and even more preferably for 4 hours to 8 hours at a culture temperature of about 25° C. by deep aeration-agitation culturing, shake culturing or static culturing and the like.

Following completion of culturing, the FAD-GDH of the present invention is collected from the culture. An ordinary known enzyme collection means may be used. For example, the enzyme can be collected by ultrasonic homogenization treatment or grinding treatment, by extracting the enzyme using a lytic enzyme such as lysozyme, or by causing the enzyme to be discharged outside the cells by lysing the cells by shaking or allowing to stand in the presence of toluene and the like. After filtering or centrifuging this solution to remove the solid portion and then removing nucleic acids by streptomycin sulfate, protamine sulfate or manganese sulfate and the like as necessary, the solution is fractionated by adding ammonium sulfate, alcohol or acetone and the like followed by collecting the precipitate to obtain crude FAD-GDH of the present invention.

The crude FAD-GDH of the present invention can be further purified by using any arbitrary known means. A sample of the purified FAD-GDH enzyme of the present invention can be obtained by, for example, gel filtration using Sephadex, Ultrogel or Bio-Gel and the like, adsorption and elution using an ion exchange resin, electrophoresis using polyacrylamide gel and the like, an adsorption and elution method using hydroxyapatite, a precipitation method such as sucrose density gradient centrifugation, affinity chromatography, a fractionation method using a molecular sieve film membrane or hollow fiber membrane and the like, or a combination thereof.

(Glucose Measurement Method Using FAD-GDH of Present Invention)

The present invention also discloses a glucose assay kit that contains the FAD-GDH of the present invention, and for example, glucose present in blood (blood sugar level) can be measured using the FAD-GDH of the present invention by using this glucose assay kit.

The glucose assay kit of the present invention contains FAD-GDH modified according to the present invention in amount at least sufficient for one assay. Typically, the glucose assay kit of the present invention contains, in addition to the modified FAD-GDH of the present invention, a buffer required for assay, a mediator, glucose standard solutions for preparing a calibration curve, and an indicator of use. The FAD-GDH modified according to the present invention can be provided in various forms, such as a freeze-dried reagent or solution in a suitable preservative solution.

In the case of a colorimetry type of glucose assay kit, glucose concentration can be measured according to that described below. A liquid or solid composition containing FAD-GDH, electron acceptor and at least one substance in the form of a reaction accelerator selected from the group consisting of N-(2-acetamide)-iminodiacetic acid (ADA), bis(2-hydroxyethyl)iminotris(hydroxymethyl)methane (Bis-Tris), sodium carbonate and imidazole are made to be retained in the reaction layer of the glucose assay kit. Here, a pH buffer and coloring reagent are added as necessary. A sample containing glucose is then added thereto and allowed to react for a fixed period of time. During this time, absorbance is monitored that is equivalent to the maximum absorption wavelength of a pigment able to polymerize and form as a result of electrons being accepted by a discoloring electron acceptor or electron acceptor due to reduction. Glucose concentration in the sample can be calculated based on the calibration curve preliminarily prepared using standard glucose concentrations from the rate of change in absorbance per unit time in the case of using a rate method, or from the change in absorbance until the time all of the glucose in the sample has been oxidized in the case of using an endpoint method.

Glucose can be quantified by adding a mediator and coloring reagent able to be used in this method in the form of, for example, 2,6-dichloroindophenol (DCIP) to serve as an electron acceptor, and then monitoring the decrease in absorbance at 600 nm. In addition, glucose concentration can be calculated by adding phenazine methosulfate (PMS) as an electron acceptor and further adding nitrotetrazolium blue (NTB) as a coloring reagent, and determining the amount of diformazan formed by measuring absorbance at 570 nm. Furthermore, it goes without saying that the electron acceptor and coloring reagent used are not limited thereto.

(Glucose Sensor Containing FAD-GDH of Present Invention)

The present invention also relates to a glucose sensor that uses the FAD-GDH of the present invention. A carbon electrode, gold electrode or platinum electrode and the like is used as an electrode, and the enzyme of the present invention is immobilized on this electrode. Examples of methods for immobilizing on the electrode include the use of a crosslinking reagent, sealing in a polymer matrix, coating with a dialysis membrane, use of a photo stabilized polymer, use of an electrically conductive polymer or use of an oxidation-reduction polymer, the enzyme of the present invention may be immobilized in a polymer or immobilized on an electrode together with an electron mediator typically represented by ferrocene or a derivative thereof, or a combination of these methods may be used. Typically, after immobilizing the modified FAD-GDH of the present invention on a carbon electrode using glutaraldehyde, the glutaraldehyde is blocked by treating with a reagent having amine groups.

Measurement of glucose concentration can be carried out in the manner described below. A buffer is placed in a constant temperature cell and maintained at a fixed temperature. Potassium ferricyanide or phenazine methosulfate and the like can be used for the mediator. An electrode immobilized with the modified FAD-GDH of the present invention is used for the working electrode along with using a counter electrode (such as a platinum electrode) and reference electrode (such as an Ag/AgCl electrode). After applying a fixed voltage to the carbon electrode and the current has reached a steady state, a sample containing glucose is added followed by measurement of the increase in current. Glucose concentration in the sample can be calculated according to a calibration curve prepared using glucose solutions having standard concentrations.

As a specific example of measurement of glucose concentration, 1.5 U of FAD-GDH are immobilized on a glassy carbon (GC) electrode followed by measuring the current response to glucose concentration. 1.8 ml of potassium phosphate buffer (pH 6.0) and 0.2 ml of 1 M aqueous potassium hexacyanoferrate (III) (potassium ferricyanide) solution are added to the electrode cell. The GC electrode is connected to a BAS100B/W potentiostat (BAS), the solution is stirred at 37° C., and +500 mV is applied to the silver-silver chloride reference electrode. 1 M D-glucose solutions are added to these systems to a final concentration of 5, 10, 20, 30, 40 and 50 mM, and the steady-state current value is measured for each addition. The current values are then plotted versus the known glucose concentrations (5, 10, 20, 30, 40 and 50 mM) to prepare a calibration curve. As a result, glucose can be quantified with an enzyme-immobilized electrode using the FAD-bound glucose dehydrogenase of the present invention.

The following provides a more detailed explanation of the present invention through examples thereof. However, the technical scope of the present invention is not limited by these examples.

EXAMPLES

1. Insertion of *Mucor*-Derived FAD-GDH into *E. coli* and Confirmation of GDH Activity An FAD-GDH gene suitable for recombination expression by *E. coli* was designed for the purpose of using *Mucor*-derived FAD-GDH as a starting material and acquired the FAD-GDH of the present invention by modification thereof. More specifically, a gene sequence was designed based on the gene sequence of *Mucor*-derived FAD-GDH of SEQ ID NO: 1 and the codon usage frequency thereof was made to be compatible with *E. coli*, followed by synthesis of the full length of that gene. The sequence of this full-length synthetic DNA is shown in SEQ ID NO: 2.

Next, an N-terminal region primer (SEQ ID NO: 3) and a C-terminal region primer (SEQ ID NO: 4) were prepared by using this full-length synthetic DNA as template, followed by inserting into the NdeI-BamHI site of pET-22b(+) vector (Novagen) according to the In-Fusion method (Clontech) to construct a recombinant plasmid (pET-22b-MpFull). This pET-22b-MpFull was then inserted into *E. coli* BL21(DE3) competent cells (Nippon Gene) by a known heat shock method. As a result of extracting the plasmid in accordance with ordinary methods and confirming the base sequence of the inserted *Mucor*-derived FAD-GDH gene, the base sequence coincided with SEQ ID NO: 2, and the amino acid residues predicted from the cDNA sequence consisted of 641 amino acids (SEQ ID NO: 1).

Moreover, the full-length sequence of the aforementioned *Mucor*-derived FAD-GDH was analyzed using a web-based signal peptide prediction program (SignalP, (www.cbs.d-tu.dk/services/SignalP-2.0/). As a result, in this FAD-GDH, it was predicted that there is the possibility of the occurrence of cleavage of a signal peptide between the 20th Ala and the 21st Gln from the N-terminal (FIG. 1). On the basis of this finding, it was hypothesized that there is the possibility of improving enzyme production volume in *E. coli* by deleting the N-terminal region up to the 20th Ala, namely the region predicted to be a signal peptide region. Therefore, a gene was acquired according to the following procedure that encodes FAD-GDH in which the region up to the 20th Ala was deleted and Met was added to the 21st Gln (referred to as NS1). Moreover, a gene was similarly acquired that encodes FAD-GDH in which the region up to the 20th Ala was deleted and the 21st Gln was substituted with Met (referred to as NS2) (FIG. 1).

First, with respect to NS 1, the oligonucleotide of SEQ ID NO: 5 was used for the N-terminal side primer, and the In-Fusion method (Clontech) was carried out by combining with the primer of SEQ ID NO: 4. Next, a recombinant plasmid having a DNA sequence encoding NS 1 (pET-22b-MpNS1) was constructed using the same procedure as that used to prepare the previously described pET-22b-MpFull, and this was inserted into *E. coli* BL21(DE3) competent cells (Nippon Gene) according to the heat shock method to acquire an *E. coli* transformant of the present invention.

In addition, with respect to NS2, an *E. coli* recombinant was similarly acquired by using the oligonucleotide of SEQ ID NO: 6 for the N-terminal side primer, and carrying out the In-Fusion method (Clontech) by combining with the primer of SEQ ID NO: 4 to construct a recombinant plasmid having a DNA sequence encoding NS2 (pET-22b-MpNS2).

Furthermore, the plasmids having DNA sequences encoding each modified FAD-GDH were confirmed to be free of sequence errors by DNA sequencing. SEQ ID NO: 7 indicates a DNA sequence that encodes the signal peptide-deficient mutant NS 1 determined as previously described. SEQ ID NO: 8 indicates the corresponding amino acid sequence thereof. SEQ ID NO: 9 indicates a DNA sequence that encodes the signal peptide-deficient mutant NS2 determined as previously described. SEQ ID NO: 10 indicates the corresponding amino acid sequence thereof.

E. coli BL21(DE3)/pET-22b-MpFull, BL21(DE3)/pET-22b-MpNS1 and BL21(DE3)/pET-22b-MpNS2 cells respectively transformed using each of the recombinant plasmids pET-22b-MpFull, pET-22b-MpNS1 and pET-22b-MpNS2 acquired as described above were inoculated into 10 mL of TY medium (1% Bacto Tryptone, 0.5% Bacto Yeast Extract, 0.5% NaCl, pH 7.0) containing 100 µg/mL of ampicillin and 1 mM IPTG, followed by shake culturing for 4 hours at 37° C. and further shake culturing overnight at 20° C.

The cultures were then subjected to one round of homogenization treatment for 10 seconds using an ultrasonic generator (Nissei) while cooling with ice. The homogenates were placed in Eppendorf tubes, and after centrifuging for 10 minutes at 12,000 rpm using a micro centrifuge, the supernatant fractions were transferred to different Eppendorf tubes and used as crude enzyme liquids. GDH activity in the resulting crude enzyme liquids was measured according to the previously described enzyme activity measurement method, and as a result of comparing GDH activity levels per 1 ml of enzyme liquid, GDH activity of E. coli transformant BL21(DE3)/pET-22b-MpFull inserted with full-length, wild-type GDH gene was only 0.0815 U/ml. On the other hand, GDH activity of 4.10 U/ml was observed in the case of E. coli transformant BL21(DE3)/pET-22b-MpNS1 inserted with modified GDH gene in which MKITAAIITVATAFASFASA of the N-terminal was deleted and M was added, while activity of 3.43 U/ml was observed in the case of E. coli transformant BL21(DE3)/pET-22b-MpNS2 inserted with modified GDH gene in which MKITAAIITVATAFASFASA of the N-terminal was deleted and M was substituted for the 21st Q. Namely, in the case of the E. coli transformants of the present invention in which a specific length of the N-terminal was deleted (BL21(DE3)/pET-22b-MpNS1 and BL21(DE3)/pET-22B-MpNS2), by deleting the amino acid sequence predicted to be the signal peptide, the GDH productivity thereof was determined to increase about 42-fold to 50-fold.

As is described above, a plurality of FAD-GDH preferable for production in E. coli were able to be acquired based on sequence information of Mucor-derived FAD-GDH. This was used as a starting material for obtaining the FAD-GDH of the present invention.

2. Measurement of FAD-GDH Activity

FAD-GDH activity was measured according to the procedure indicated below.

More specifically, first in Reaction 1, PMS (reduced form) is produced accompanying oxidation of D-glucose. As a result of the subsequent Reaction 2, DCIP is reduced accompanying oxidation of PMS (reduced form). The degree of consumption of this DCIP (oxidized form) can be detected as the amount of change in absorbance at a wavelength of 600 nm, and enzyme activity can be determined based on this amount of change.

More specifically, flavin-binding GDH activity can be measured according to the procedure indicated below. 2.05 mL of 50 mM phosphate buffer (pH 6.5), 0.6 mL of 1 M D-glucose solution and 0.15 mL of 2 mM DCIP solution are mixed followed by warming for 5 minutes at 37° C. Next, 0.1 mL of 15 mM PMS solution and 0.1 mL of enzyme sample solution are added to start the reaction. Absorbance is measured at the start of the reaction and over time, the amount of the reduction in absorbance at 600 nm per minute ($\Delta A600$) is determined as the enzyme reaction proceeds, and flavin-binding GDH activity is calculated according to the following equation. At this time, 1 U of flavin-binding GDH activity is defined as the amount of enzyme that reduces 1 µmol of DCIP in 1 minute in the presence of D-glucose at a concentration of 200 mM at 37° C.

$$GDH \text{ activity (U/ml)} = \frac{-(\Delta A600 - \Delta A600_{blank}) \times 3.0 \times df}{16.3 \times 0.1 \times 1.0} \quad \text{[Equation 2]}$$

Furthermore, the value of 3.0 in the equation represents the liquid volume (mL) of the reaction reagents and enzyme sample, the value of 16.3 represents the millimolar molecular extinction coefficient ($cm^2/\mu mol$) under the activity measurement conditions, the value of 0.1 represents the liquid volume (mL) of the enzyme solution, the value of 1.0 represents the cell path length (cm), $\Delta 600_{blank}$ represents the reduction in absorbance at 600 nm per minute in the case of initiating the reaction by adding 10 mM acetate buffer (pH 5.0) instead of enzyme sample solution, and df represents the dilution factor.

3. Evaluation of Heat Stability of FAD-GDH

Heat stability of FAD-GDH was evaluated based on residual activity following heat treatment under prescribed conditions carried out prior to using in the aforementioned measurement of FAD-GDH activity. More specifically, the evaluated FAD-GDH was diluted with enzyme diluent (10 mM acetate buffer, pH 5.0) to about 0.5 U/ml. Two aliquots of this enzyme solution (0.2 ml) were prepared, and one of the aliquots was stored at 4° C. while the other was subjected to heat treatment for 10 minutes at 35° C.

Following heat treatment, the FAD-GDH activity of each sample was measured and the activity level after heat treatment for 10 minutes at 35° C. based on a value of 100 for the enzyme activity of the enzyme solution stored at 4° C. was calculated as residual activity (%). This residual activity was used as an indicator for evaluating heat resistance of each FAD-GDH.

4. Preparation and Modification of Recombinant Plasmid pET-22b-MpNS1 DNA

E. coli strain BL21(DE3)/pET-022b-MpNS1 having a recombinant plasmid of Mucor-derived FAD-GDH gene (SEQ ID NO: 7) was inoculated into 100 ml of LB-amp medium (1% (w/v) Bacto Tryptone, 0.5% (w/v) peptone, 0.5% (w/v) NaCl, 50 µg/ml of ampicillin) followed by shake culturing for 20 hours at 37° C. to obtain a culture.

Bacterial cells were collected by centrifuging this culture for 5 minutes at 9,000 rpm. Recombinant plasmid pET-22b-MpNS1 was extracted from the cells and purified using Qiagen Tip-100 (Qiagen) to obtain 100 µg of recombinant plasmid pET-22b-MpNS1.

XL1-RED (Stratagene, susceptible to the occurrence of plasmid replication errors and modification during proliferation) was transformed using 20 µg of the 100 µg of the resulting recombinant plasmid pET-22b-MpNS1 in accordance with the method of D. M. Morrison (Method in Enzymology, 68, 326-331, 1979) to obtain about 5,000 strains of transformants.

Qiagen Sol I (Qiagen) was added to agar medium to recover plasmid DNA from all colonies, the colonies were scraped together with the Qiagen Sol I using a spreader, the solution was recovered with a Pipetman, and the remainder of the procedure was carried out in the same manner as ordinary plasmid recovery methods to obtain 100 µg of modified recombinant plasmid pET-22b-MpNS1 DNA. *E. coli* BL21 (DE3) competent cells (Nippon Gene) were then transformed using 20 µg of the aforementioned modified recombinant plasmid pET-22b-MpNS1 in accordance with the method of D. M. Morrison (Method in Enzymology, 68, 326-331, 1979) to obtain about 1,000 strains of transformants retaining plasmids subjected to modification.

5. Search for Modified FAD-GDH Having Superior Heat Stability

The various transformants obtained in the manner described above were inoculated into LB-amp medium (1% (w/v) Bacto Tryptone, 0.5% (w/v) peptone, 0.5% (w/v) NaCl, 50 µg/ml of ampicillin) containing 1 mM IPTG followed by shake culturing overnight at 20° C. Cells obtained by centrifuging (9,000 rpm, 5 minutes) a portion of that culture were recovered in 10 mM acetate buffer (pH 5.0) and after subjecting to ultrasonic homogenization in accordance with ordinary methods, were centrifuged for 10 minutes at 5,000 rpm to prepare a supernatant (crude enzyme liquid). Residual activity (%) (activity after treatment/activity before treatment) was then calculated in accordance with the aforementioned method for evaluating heat stability using this crude enzyme liquid.

As a result, three types of FAD-GDH of the present invention were acquired that had improved residual activity in comparison with FAD-GDH derived from transformants containing pET-22b-MpNS1 that were not subjected to mutagenic treatment. Plasmids encoding these three types of FAD-GDH were designated as pET-22b-MpNS1-M1, pET-22b-MpNS1-M2 and pET-22b-MpNS1-M3, and the base sequence of DNA encoding FAD-GDH in each plasmid was determined using the CEQ2000 Multi Capillary DNA Analysis System (Beckman Coulter). As a result, mutations were determined to have been inserted in which alanine was substituted for the 213th valine of the amino acid described in SEQ ID NO: 8 in pET-22b-MpNS1-M1, alanine was substituted for the 368th threonine of the amino acid sequence described in SEQ ID NO: 8 pET-22b-MpNS1-M2, and valine was substituted for the 526th isoleucine of the amino acid sequence described in SEQ ID NO: 8 in pET-22b-MpNS1-M3. The results are shown in Table 1.

TABLE 1

| Plasmid | Amino acid substitution | Residual activity (%) |
| --- | --- | --- |
| pET-22b-MpNS1-M1 | V213A | 12.5 |
| pET-22b-MpNS1-M2 | T368A | 100 |
| pET-22b-MpNS1-M3 | I526V | 3.4 |
| pET-22b-MpNS1 | (wild type) | 2.1 |

6. Additional Acquisition of FAD-GDH of Present Invention by Site-Specific Mutagenesis Next, the aforementioned three locations of amino acid residue substitutions were attempted to be respectively substituted with other amino acids based on the previously described findings. More specifically, mutagenesis was carried out using the Quick Change Site-Directed Mutagenesis Kit (Stratagene) in accordance with the protocol thereof using pET-22b-MpNS1 plasmid as template based on the synthetic oligonucleotides of SEQ ID NO: 11 and 12 designed to as to substitute multiple types of amino acids for the 213th valine, the synthetic oligonucleotides of SEQ ID NO: 13 and 14 designed so as to substitute multiple types of amino acids for the 368th threonine, and the synthetic oligonucleotides of SEQ ID NO: 15 and 16 designed so as to substitute multiple types of amino acids for the 526th isoleucine, and various types of modified FAD-GDH mutant plasmids were prepared in compliance with the aforementioned method. After transforming commercially available *E. coli* BL21(DE3) competent cells (Nippon Gene) with the resulting plasmids, crude enzyme liquids were prepared in compliance with the aforementioned method followed by evaluation of heat stability.

As a result, an additional 17 types of mutants having improved heat stability were obtained. The plasmids encoding these 17 types of mutants were designated as pET-22b-MpNS1-M4, pET-22b-MpNS1-M5, pET-22b-MpNS1-M6, pET-22b-MpNS1-M7, pET-22b-MpNS1-M8, pET-22b-MpNS1-M9, pET-22b-MpNS1-M10, pET-22b-MpNS1-M11, pET-22b-MpNS1-M12, pET-22b-MpNS1-M13, pET-22b-MpNS1-M14, pET-22b-MpNS1-M15, pET-22b-MpNS1-M16, pET-22b-MpNS1-M17, pET-22b-MpNS1-M18, pET-22b-MpNS1-M19 and pET-22b-MpNS1-M20. As a result of determining the base sequences of genes encoding glucose dehydrogenase using the CEQ2000 Multi Capillary DNA Analysis System (Beckman Coulter) in order to identify the locations of mutations in each of these mutants, valine for the 368th threonine described in SEQ ID NO: 8 in pET-22b-MpNS1-M4, glycine for the 368th threonine described in SEQ ID NO: 8 in pET-22b-MpNS1-M5, serine for the 368th threonine in pET-22b-MpNS1-M6, cysteine for the 368th threonine in pET-22b-MpNS1-M7, threonine for the 526th isoleucine in pET-22b-MpNS1-M8, serine for the 526th isoleucine in pET-22b-MpNS1-M9, proline for the 526th isoleucine in pET-22b-MpNS1-M10, alanine for the 526th isoleucine in pET-22b-MpNS1-M11, tyrosine for the 526th isoleucine in pET-22b-MpNS1-M12, lysine for the 526th isoleucine in pET-22b-MpNS1-M13, histidine for the 526th isoleucine in pET-22b-MpNS1-M14, phenylalanine for the 526th isoleucine in pET-22b-MpNS1-M15, glutamic acid for the 526th isoleucine in pET-22b-MpNS1-M16, methionine for the 213th valine in pET-22b-MpNS1-M17, cysteine for the 213th valine in pET-22b-MpNS1-M18, glutamine for the 213th valine in pET-22b-MpNS1-M19, and glutamic acid for the 213th valine in pET-22b-MpNS1-M20, were confirmed to have been substituted.

Data relating to the amino acid substitutions and heat stability of the 20 types of mutants, including the additionally discovered mutants, is shown in Table 2.

TABLE 2

| Plasmid | Amino acid substitution | Residual activity (%) |
| --- | --- | --- |
| pET-22b-MpNS1-M1 | V213A | 12.5 |
| pET-22b-MpNS1-M17 | V213M | 27.5 |
| pET-22b-MpNS1-M18 | V213C | 6.3 |
| pET-22b-MpNS1-M19 | V213Q | 8.7 |
| pET-22b-MpNS1-M20 | V213E | 50.9 |
| pET-22b-MpNS1-M2 | T368A | 100 |
| pET-22b-MpNS1-M4 | T368V | 3.1 |
| pET-22b-MpNS1-M5 | T368G | 22.3 |
| pET-22b-MpNS1-M6 | T368S | 46.4 |
| pET-22b-MpNS1-M7 | T368C | 81.6 |
| pET-22b-MpNS1-M3 | I526V | 3.4 |
| pET-22b-MpNS1-M8 | I526T | 46.7 |
| pET-22b-MpNS1-M9 | I526S | 29.4 |
| pET-22b-MpNS1-M10 | I526P | 33.0 |
| pET-22b-MpNS1-M11 | I526A | 9.0 |
| pET-22b-MpNS1-M12 | I526Y | 4.4 |
| pET-22b-MpNS1-M13 | I526K | 3.7 |
| pET-22b-MpNS1-M14 | I526H | 4.8 |
| pET-22b-MpNS1-M15 | I526F | 3.9 |
| pET-22b-MpNS1-M16 | I526E | 6.9 |

As shown in Table 2, heat stability was determined to improve by substituting alanine for the 213th valine, substituting methionine for the 213th valine, substituting cysteine for the 213th valine, substituting glutamine for the 213th valine, substituting glutamic acid for the 213th valine, substituting alanine for the 368th threonine, substituting valine for the 368th threonine, substituting glycine for the 368th threonine, substituting serine for the 368th threonine, substituting cysteine for the 368th threonine, substituting valine for the 526th isoleucine, substituting threonine for the 526th isoleucine, substituting serine for the 526th isoleucine, substituting proline for the 526th isoleucine, substituting alanine for the 526th isoleucine, substituting tyrosine for the 526th isoleucine, substituting lysine for the 526th isoleucine, substituting histidine for the 526th isoleucine, substituting phenylalanine for the 526th isoleucine or substituting glutamic acid for the 526th isoleucine of SEQ ID NO: 1.

7. Further Improvement of Heat Stability by Accumulation of Site-Specific Mutations PCR reactions were carried out using KOD-Plus- (Toyobo) under the following conditions using plasmid pET-22b-MpNS1-M8 containing the mutation I526T as template based on the synthetic oligonucleotides of SEQ ID NO. 17 and 18 designed so that alanine is substituted for the 368th threonine.

Namely, 5 µl of 10×KOD-Plus- buffer, 5 µl of a mixed solution of dNTPs prepared so that the concentration of each dNTP was 2 mM, 2 µl of 25 mM MgSO$_4$, 50 ng of pET-22b-MpNS1-M8 DNA serving as template, 15 pmol of each of the aforementioned synthetic oligonucleotides and 1 unit of KOD-Plus- were added followed by the addition of sterile water to bring to a total volume of 50 µl and prepare a reaction liquid. This reaction liquid was incubated for 2 minutes at 94° C. followed by repeating 30 cycles consisting of 15 seconds at 94° C., 30 seconds at 50° C. and 7 minutes 30 seconds at 68° C. using a thermal cycler (Eppendorf).

A portion of the reaction liquid was electrophoresed using 1.0% agarose gel to confirm that DNA of the target length is specifically amplified. The resulting DNA was treated using restrictase DpnI (New England Biolabs), and after having cleaved the remaining template DNA, was used to transform E. coli strain BL21(DE3) followed by transferring to LB-amp agar medium. The colonies that formed were inoculated into LB-amp medium followed by shake culturing and isolating the plasmid DNA using the same method as previously described. The base sequence of DNA that encoded GDH in the plasmid was determined using the CEQ2000 Multi Capillary DNA Analysis System (Beckman Coulter), and a recombinant plasmid was acquired that encoded modified GDH in which alanine was substituted for the 368th threonine and threonine was substituted for the 526th isoleucine in the amino acid sequence described in SEQ ID NO: 8 (pET-22b-MpNS1-M21).

Continuing, a recombinant plasmid was acquired that encodes modified GDH in which glutamic acid is substituted for the 213th valine and alanine is substituted for the 368th threonine in the amino acid sequence of SEQ ID NO: 8 (pET-22b-MpNS1-M22) by carrying out the same procedure as described above using plasmid pET-22b-MpNS1-M20 containing the mutation V213E as template and using the synthetic oligonucleotides of SEQ ID NO: 17 and 18 designed so that alanine is substituted for the 368th threonine.

Continuing, a recombinant plasmid was acquired that encodes modified GDH in which glutamic acid is substituted for the 213th valine and alanine is substituted for the 368th threonine in the amino acid sequence of SEQ ID NO: 8 (pET-22b-MpNS1-M23) by carrying out the same procedure as described above using plasmid pET-22b-MpNS1-M22 containing the mutations V213E and T368A as template and using the synthetic oligonucleotides of SEQ ID NO: 48 and 49 designed so that threonine is substituted for the 526th isoleucine.

Continuing, crude enzyme liquids were prepared in compliance with the aforementioned section 5 for E. coli strain BL21(DE3) retaining each of the recombinant plasmids pET-22b-MpNS1-M2, pET-22b-MpNS1-M8, pET-22b-MpNS1-M20, pET-22b-MpNS1-M21, pET-22b-MpNS1-M22 and pET-22b-MpNS1-M23 obtained according to the procedures described above, and residual activities (%) were calculated after subjecting to heat treatment at 40° C. for 15 minutes and at 45° C. for 15 minutes using the heat treatment step of the heat stability and activity measurement method previously described. The results are shown in Table 3.

TABLE 3

| Plasmid | Amino acid substitution | Residual activity (%) 40° C. | 45° C. |
|---|---|---|---|
| pET-22b-MpNS1-M20 | V213E | 0.5 | 0 |
| pET-22b-MpNS1-M2 | T368A | 15.9 | 0 |
| pET-22b-MpNS1-M8 | I526T | 0.7 | 0 |
| pET-22b-MpNS1-M21 | T368A/I526T | 62.3 | 4.4 |
| pET-22b-MpNS1-M22 | V213E/T368A | 91.4 | 14.8 |
| pET-22b-MpNS1-M23 | V213E/T368A/I526T | 100 | 68.1 |
| pET-22b-MpNS1 | (wild type) | 0.3 | 0 |

As shown in Table 3, heat stability was confirmed to further improve as a result of combining multiple mutation locations and accumulating site-specific mutations.

8. Evaluation of Heat Stability of Mucor-Derived FAD-GDH in Yeast Expression System (1) Preparation of Yeast Transformant Sc-Mp Expressing Mucor-Derived FAD-GDH A recombinant plasmid (puc-MGD) was acquired that contains the FAD-GDH gene of SEQ ID NO: 23 (described as MpGDH gene is Patent Document 5) encoding the amino acid sequence described in SEQ ID NO: 1 in compliance with the method described in Patent Document 5. A PCR reaction was carried out in accordance with the protocol provided using this as template and using the synthetic nucleotides of SEQ ID NO: 24 and 25 by using Prime Star Max DNA Polymerase (Takara). The PCR reaction liquid was electrophoresed in 1.0% agarose gel, and an approximately 2 kb insert DNA fragment was purified using Recochip (Takara).

In addition, plasmid pYES2/CT for expression in Saccharomyces cerevisiae (Invitrogen) was treated with restrictase KpnI (New England Biolabs), the reaction liquid obtained following restrictase treatment was electrophoresed in 1.0% agarose gel, and an approximately 6 kb vector DNA fragment was purified using Recochip (Takara).

Continuing, the purified insert DNA fragment and vector DNA fragment were coupled in accordance with the protocol provided using the In-Fusion HD Cloning Kit (Clontech) to prepare recombinant plasmid pYE2C-Mp for expressing MpGDH under the control of GAL1 promoter. Furthermore, GAL1 promoter is a D-galactose-inducible promoter that contains D-galactose and induces gene expression downstream from the promoter as a result of culturing in medium not containing D-galactose. This pYES2C-Mp was confirmed to encode the gene sequence of SEQ ID NO: 2 with the CEQ2000 Multi Capillary DNA Analysis System (Beckman Coulter). Subsequently, yeast transformant strain Sc-Mp expressing the Mucor-derived FAD-GDH of SEQ ID NO: 1 was acquired by transforming strain Inv-Sc (Invitrogen) with pYE2C-Mp using an S. cerevisiae transformation kit (Invitrogen).

(2) Conformation of GDH Activity and Evaluation of Heat Stability in Strain Sc-Mp Yeast transformant strain Sc-Mp was cultured for 24 hours at 30° C. in 5 mL of pre-culture liquid medium (containing 0.67% (w/v) of amino acid-free yeast nitrogen base (BD), 0.192% (w/v) of uracil-free yeast synthesis dropout medium additive (Sigma), and 2.0% (w/v) of raffinose). Subsequently, 1 mL of the pre-culture liquid was added to 4 mL of final culture liquid medium (containing 0.67% (w/v) of amino acid-free yeast nitrogen base, 0.192% (w/v) of uracil-free yeast synthesis dropout medium additive, 2.5% (w/v) D-galactose, and 0.75% (w/v) raffinose) followed by culturing for 16 hours at 30° C. This culture liquid was separated into cells and culture supernatant by centrifugation (10,000×g, 4° C., 3 minutes), and GDH activity was confirmed to be present in the culture supernatant when GDH activity was measured according to the enzyme activity measurement method previously described.

Next, when activity was measured after heat treatment for 15 minutes at 50° C. based on the method for evaluating heat stability described in the aforementioned Section 3 using this culture supernatant fraction, residual ability was determined to be 4.3%.

9. Verification of Effect of Improving Heat Stability in Yeast Expression System Mutations for improving heat stability discovered in the manner described above were introduced at the sites equivalent to SEQ ID NO: 1 to verify the effect of improving heat stability in a yeast expression system. Furthermore, those portions of the aforementioned mutation sites for improving heat stability of V213, T368 and I526 equivalent to SEQ ID NO:1 are V232, T387 and I545, respectively.

PCR reactions were carried out under the following conditions using recombinant plasmid pYE2C-Mp as template and the synthetic nucleotides of SEQ ID NO: 26 and 27 by using KOD-Plus- (Toyobo).

Namely, 5 µl of 10×KOD-Plus- buffer, 5 µl of a mixed solution of dNTPs prepared so that the concentration of each dNTP was 2 mM, 2 µl of 25 mM $MgSO_4$, 50 ng of pYE2C-Mp serving as template, 15 pmol of each of the aforementioned synthetic oligonucleotides and 1 unit of KOD-Plus- were added followed by bringing to a final volume of 50 µl with sterile water. The prepared reaction liquid was incubated for 2 minutes at 94° C. followed by repeating 30 cycles consisting of 15 seconds at 94° C., 30 seconds at 55° C. and 8 minutes at 68° C. using a thermal cycler (Eppendorf).

A portion of the reaction liquid was electrophoresed in 1.0% agarose gel to confirm that DNA of approximately 8 kbp is specifically amplified. The resulting DNA was treated using restrictase DpnI (New England Biolabs) followed by carrying out transformation by mixing with competent cells of *E. coli* strain JM109 (Nippon Gene) in accordance with the protocol provided, and applying to LB-amp agar medium. The colonies that formed were inoculated into LB-amp liquid medium followed by shake culturing and isolating the plasmid DNA using the GenElute Plasmid Miniprep Kit (Sigma) in accordance with the protocol provided. The base sequence of DNA that encoded FAD-GDH in the plasmid was determined using the CEQ2000 Multi Capillary DNA Analysis System (Beckman Coulter), and a recombinant plasmid was acquired that encoded modified *Mucor*-derived FAD-GDH in which alanine was substituted for the 232nd valine in the amino acid sequence described in SEQ ID NO: 8 (pYE2C-Mp-V232A).

PCR reactions were similarly carried out by combining the template plasmids and synthetic nucleotides having the sequence ID numbers shown in Table 4, *E. coli* strain JM109 was transformed using vectors containing amplified DNA, and the base sequences of DNA encoding *Mucor*-derived FAD-GDH in the plasmid DNA retained by the formed colonies were determined to acquire recombinant plasmids consisting of pYE2C-Mp-V232C, pYE2C-Mp-V232M, pYE2C-Mp-V232Q, pYE2C-Mp-V232E, pYE2C-Mp-T387A, pYE2C-Mp-T387C, pYE2C-Mp-T387S, pYE2C-Mp-T387G, pYE2C-Mp-I545T, pYE2C-Mp-I545S, pYE2C-Mp-T387A/I545T and pYE2C-Mp-V232E/T387A/I545T in which cysteine for the 232nd valine, methionine for the 232nd valine, glutamine for the 232nd valine, glutamic acid for the 232nd valine, alanine for the 387th threonine, cysteine for the 387th threonine, serine for the 387th threonine, glycine for the 387th threonine, threonine for the 545th isoleucine, serine for the 545th isoleucine, proline for the 545th isoleucine, alanine for the 387th threonine and threonine for the 545th isoleucine, and glutamic acid for the 232nd valine, alanine for the 387th threonine and threonine for the 545th isoleucine, were respectively substituted in the amino acid sequence described in SEQ ID NO: 1.

Strain Inv-Sc was transformed and transformants were cultured in the same manner as previously described using recombinant plasmids pYE2C-Mp-V232A, pYE2C-Mp-V232C, pYE2C-Mp-V232M, pYE2C-Mp-V232Q, pYE2C-Mp-V232E, pYE2C-Mp-T387A, pYE2C-Mp-T387C, pYE2C-Mp-T387S, pYE2C-Mp-T387G, pYE2C-Mp-I545T, pYE2C-Mp-I545S, pYE2C-Mp-T387A/I545T and pYE2C-Mp-V232E/T387A/I545T encoding modified *Mucor*-derived FAD-GDH containing site-specific mutations as previously described, followed by measurement of FAD-GDH activity in the culture supernatant.

Continuing, residual activities after subjecting to heat treatment for 15 minutes at 50° C. and 15 minutes at 55° C. were measured based on the method for evaluating heat stability of the aforementioned Section 3 using the culture supernatant of each of the aforementioned mutants for which GDH activity was confirmed. The results are shown in Table 4. Furthermore, the "-" symbol in the table indicates that data was not acquired.

TABLE 4

| Template | Primer sequence number | Amino acid substitution | Residual activity (%) 50° C. | Residual activity (%) 55° C. |
|---|---|---|---|---|
| — | — | wild type | 4.3 | 0.0 |
| pYE2C-Mp | 26, 27 | V232A | 8.3 | — |
|  | 28, 27 | V232C | 9.3 | — |
|  | 29, 27 | V232M | 33.4 | — |
|  | 30, 27 | V232Q | 20.8 | — |
|  | 31, 27 | V232E | 43.5 | 3.6 |
|  | 32, 33 | T387A | 60.5 | 14.3 |
|  | 34, 33 | T387C | 73.3 | — |
|  | 35, 33 | T387S | 21.9 | — |
|  | 36, 33 | T387G | 10.6 | — |
|  | 37, 38 | I545T | 68.9 | 26.3 |
|  | 39, 38 | I545S | 7.7 | — |
|  | 40, 38 | I545P | — | — |
| pYE2C-Mp-T387A | 37, 38 | T387A/I545T | 71.2 | 27.0 |
| pYE2C-Mp-T387A/I545T | 31, 27 | V232E/T387A/I545T | 82.8 | 63.9 |

On the basis thereof, substitutions at sites equivalent to position V232, position T387 and position I545 were determined to demonstrate effects that improve heat stability irrespective of the presence or absence of a signal sequence.

As shown in Table 4, site-specific mutagenesis at position V232, position T387 and position I545 in the FAD-GDH of SEQ ID NO: 1 was confirmed to improve heat resistance in a yeast expression system. In addition, heat resistance was confirmed to be further improved in V232E/T387A/I545T in which mutations were accumulated.

10. Accumulation of Mutations for Improving Substrate Specificity in Mutants Having Improved Heat Resistance (1) Substrate Specificity Evaluation Method First, culture supernatant fractions of each *Mucor*-derived FAD-GDH-expressing yeast strain were acquired in the same manner as described in the aforementioned Section 8 followed by measurement of GDH activity. Next, activity was measured in a system in which an equimolar concentration of D-xylose was used for the substrate of the activity measurement method of Section 3 instead of D-glucose. The ratio of the reactivity to D-xylose to the reactivity to D-glucose (Xyl/Glc (%)) was calculated based on these measured values and this ratio was used to evaluate substrate specificity. At this time, substrate specificity can be judged to be better the lower the ratio of Xyl/Glc (%).

(2) Acquisition of FAD-GDH-Expressing Yeast Strains Containing Mutation that Improves Heat Resistance and Mutation that Improves Substrate Specificity Those mutations that improve substrate specificity previously discovered by the inventors were introduced into pYE2C-Mp-V232E/T387A/I545T. Namely, mutations for improving substrate specificity in the form of L121M, W569Y, S612C and S612T were introduced into pYE2C-Mp-V232E/T387A/I545T in which mutation V232E/T387A/I545T was introduced in SEQ ID NO: 1.

PCR reactions were carried out under the following conditions using recombinant plasmid pYE2C-Mp-V232E/T387A/I545T as template and using the synthetic nucleotides of SEQ ID NO: 41 and 42 by using KOD-Plus- (Toyobo).

Namely, 5 μl of 10×KOD-Plus- buffer, 5 μl of a mixed solution of dNTPs prepared so that the concentration of each dNTP was 2 mM, 2 μl of 25 mM $MgSO_4$, 50 ng of pYE2C-Mp-V232E/T387A/I545T serving as template, 15 pmol of each of the aforementioned synthetic oligonucleotides and 1 unit of KOD-Plus- were added followed by bringing to a final volume of 50 μl with sterile water. The prepared reaction liquid was incubated for 2 minutes at 94° C. followed by repeating 30 cycles consisting of 15 seconds at 94° C., 30 seconds at 55° C. and 8 minutes at 68° C. using a thermal cycler (Eppendorf).

A portion of the reaction liquid was electrophoresed in 1.0% agarose gel to confirm that DNA of approximately 8 kbp is specifically amplified. The resulting DNA was treated with restrictase DpnI (New England Biolabs) followed by carrying out transformation by mixing with competent cells of *E. coli* strain JM109 (Nippon Gene) in accordance with the protocol provided, and applying to LB-amp agar medium. The colonies that formed were inoculated into LB-amp liquid medium followed by shake culturing and isolating the plasmid DNA using the GenElute Plasmid Miniprep Kit (Sigma) in accordance with the protocol provided. The base sequence of DNA that encoded FAD-GDH in the plasmid was determined using the CEQ2000 Multi Capillary DNA Analysis System (Beckman Coulter), and a recombinant plasmid was acquired that encoded modified *Mucor*-derived FAD-GDH in which methionine for the 121st leucine, as well as glutamic acid for the 232nd valine, alanine for the 387th threonine and threonine for the 545th isoleucine, were substituted in the amino acid sequence described in SEQ ID NO: 1 (pYE2C-Mp-3T-L121M).

PCR reactions were similarly carried out using pYE2C-Mp-V232E/T387A/I545T as template by combining the synthetic nucleotides having the sequence ID numbers shown in Table 5, *E. coli* strain JM109 was transformed using vectors containing amplified DNA, and the base sequences of DNA encoding *Mucor*-derived FAD-GDH in the plasmid DNA retained by the formed colonies were determined to acquire recombinant plasmids consisting of pYE2C-Mp-3T-W569Y, pYE2C-Mp-3T-S612C and pYE2C-Mp-3T-S612T in which glutamic acid for valine at position 232, alanine for threonine at position 387 and threonine for isoleucine at position 545, as well as tyrosine for tryptophan at position 569, cysteine for serine at position 612 or threonine for serine at position 612, were respectively substituted in the amino acid sequence described in SEQ ID NO: 1.

Strain Inv-Sc was transformed and transformants were cultured in the same manner as previously described using recombinant plasmids pYE2C-Mp-3T-L121M, pYE2C-Mp-3T-W569Y, pYE2C-Mp-3T-S612C and pYE2C-Mp-3T-S612T encoding modified *Mucor*-derived FAD-GDH containing site-specific mutations as previously described, followed by confirmation of the presence of GDH activity in the culture supernatant.

(3) Evaluation of FAD-GDH Containing Mutations for Improving Heat Resistance and Substrate Specificity Continuing, residual activities after subjecting to heat treatment for 15 minutes at 55° C. and 15 minutes at 60° C. were measured based on the aforementioned method for evaluating heat stability using the culture supernatant of each of the mutants for which GDH activity was confirmed. Moreover, the ratios of Xyl/Glc (%) were measured based on the substrate specificity evaluation method described in (1) above. The results are shown in Table 5.

TABLE 5

| Amino acid substitution | Primer sequence number | Residual activity (%) 55° C. | Residual activity (%) 60° C. | Xyl/Glc (%) |
|---|---|---|---|---|
| V232E/ T387A/ I545T | — | — | 63.9 | 18.2 | 2.0 |
| | L121M | 41, 42 | 7.8 | 0 | 2.4 |
| | W569Y | 43, 44 | 74.8 | 55.4 | 0.8 |
| | S612C | 45, 46 | 67.7 | 14.5 | 1.6 |
| | S612T | 47, 46 | 61.3 | 19.4 | 1.5 |

As shown in Table 5, modified *Mucor*-derived FAD-GDH in which W569Y, S612C or S612T was introduced into V232E/T387A/I545T demonstrated improved substrate specificity in comparison with V232E/T387A/I545T. In addition, modified *Mucor*-derived FAD-GDH in which W569Y was introduced into V232E/T387A/I545T also demonstrated improved heat resistance in comparison with V232E/T387A/I545T.

11. Preparation and Evaluation of Yeast Strain Expressing Modified FAD-GDH

A strain of *Aspergillus* sojae was acquired that expresses FAD-GDH in which the mutation V232E/T387A/I545T/W569Y has been introduced into the amino acid sequence of SEQ ID NO: 1 as described in Patent Document 5, followed by culturing and confirmation of GDH activity of the crude enzyme liquid. When activity after subjecting to heat treatment for 15 minutes at 55° C. was measured based on the previously described method for evaluating heat stability using this crude enzyme liquid, in contrast to FAD-GDH activity prior to mutagenesis being 0%, residual activity of FAD-GDH containing the mutation V232E/T387A/I545T/W569Y was 87.2%, thus demonstrating improvement of heat stability. In addition, when Xyl/Glc ratio (%) was measured based on the method described in Section 10 using the same crude enzyme liquid, in contrast to the ratio in FAD-GDH prior to mutagenesis being 1.41%, the ratio in FAD-GDH containing the mutation V232E/T387A/I545T/W569Y was 0.64%, thus demonstrating improved substrate specificity.

As a result of having adequate heat stability and a low degree of heat-induced enzyme deactivation, the mutants of the present invention are expected to be able to reduce the amount of enzyme used and extend the shelf life thereof, thereby making it possible to provide assay methods, assay reagents and assay kits or sensors having greater practicality in comparison with assay methods and assay reagents using known glucose assay enzymes. In particular, the FAD-GDH of the present invention having superior heat stability is considered to be extremely useful in the production process of blood sugar sensor chips during which the chips are likely to be subjected to heating and drying treatment. In addition, since the various types of mutants of the present invention that result in improved heat stability are derived from a wild type prior to mutagenesis and have high substrate specificity for glucose in the same manner as the *Mucor*-derived FAD-GDH described in Japanese Patent No. 4648993 previously discovered by the inventors of the present invention, they enable glucose measured values to be measured accurately even under conditions in which there is contamination by sugar compounds such as maltose, D-galactose or D-xylose.

Sequence Listing

Sequences

The invention claimed is:

1. A flavin-binding glucose dehydrogenase consisting of the amino acid sequence indicated in SEQ ID NO: 8, or an amino acid sequence having sequence identity with that amino acid sequence of 90% or more; and, characterized by having one or more amino acid substitutions selected from the group consisting of:
   valine at position 213 in the amino acid sequence described in SEQ ID NO: 8 or an amino acid residue equivalent thereto,
   threonine at position 368 in the amino acid sequence described in SEQ ID NO: 8 or an amino acid residue equivalent thereto,
   and isoleucine at position 526 in the amino acid sequence described in SEQ ID NO: 8 or an amino acid residue equivalent thereto.

2. The flavin-binding glucose dehydrogenase according to claim 1, characterized by having one or more amino acid substitutions selected from the group consisting of:
   valine at position 232 in the amino acid sequence described in SEQ ID NO: 1,
   threonine at position 387 in the amino acid sequence described in SEQ ID NO: 1, and
   isoleucine at position 545 in the amino acid sequence described in SEQ ID NO: 1.

3. A flavin-binding glucose dehydrogenase gene encoding the flavin-binding glucose dehydrogenase according to claim 1.

4. A vector containing the flavin-binding glucose dehydrogenase gene according to claim 3.

5. A host cell containing the vector according to claim 4.

6. A method for producing a flavin-binding glucose dehydrogenase, comprising the following steps:
   culturing the host cell according to claim 5,
   expressing a flavin-binding glucose dehydrogenase gene contained in the host cell, and
   recovering the flavin-binding glucose dehydrogenase from the culture.

7. A method for measuring glucose using the flavin-binding glucose dehydrogenase according to claim 1.

8. A glucose assay kit characterized by containing the flavin-binding glucose dehydrogenase according to claim 1.

9. A glucose sensor characterized by containing the flavin-binding glucose dehydrogenase according to claim 1.

10. A flavin-binding glucose dehydrogenase gene encoding the flavin-binding glucose dehydrogenase according to claim 2.

11. A flavin-binding glucose dehydrogenase consisting of the amino acid sequence indicated in SEQ ID NO: 8, or an amino acid sequence having sequence identity with that amino acid sequence of 90% or more, and, characterized by having one or more amino acid substitutions at positions corresponding to amino acids selected from the group consisting of:
the amino acid residue at a position equivalent to position 213 in the amino acid sequence described in SEQ ID NO: 8 is alanine, methionine, cysteine, glutamine or glutamic acid,
the amino acid residue at a position equivalent to position 368 in the amino acid sequence described in SEQ ID NO: 8 is alanine, valine, glycine, serine or cysteine, and
the amino acid residue at a position equivalent to position 526 in the amino 35 acid sequence described in SEQ ID NO: 8 is valine, threonine, serine, proline, alanine, tyrosine, lysine, histidine, phenylalanine or glutamic acid.

12. The flavin-binding glucose dehydrogenase according to claim 11, characterized by having one or more amino acid substitutions at positions corresponding to amino acids selected from the group consisting of:
the amino acid residue at a position equivalent to position 232 in the amino acid sequence described in SEQ ID NO: 1 is alanine, methionine, cysteine, glutamine or glutamic acid,
the amino acid residue at a position equivalent to position 387 in the amino acid sequence described in SEQ ID NO: 1 is alanine, valine, glycine, serine or cysteine, and
the amino acid residue at a position equivalent to position 545 in the amino acid sequence described in SEQ ID NO: 1 is valine, threonine, serine, proline, alanine, tyrosine, lysine, histidine, phenylalanine or glutamic acid.

13. A flavin-binding glucose dehydrogenase gene encoding the flavin-binding glucose dehydrogenase according to claim 11.

14. A flavin-binding glucose dehydrogenase gene encoding the flavin-binding glucose dehydrogenase according to claim 12.

15. A flavin-binding glucose dehydrogenase gene selected from the group consisting of:
a DNA encoding the amino acid sequence indicated in SEQ ID NO: 8,
a DNA consisting of the base sequence indicated in SEQ ID NO.: 9,
a DNA encoding the amino acid sequence indicated in SEQ ID NO: 10, and
a DNA having a base sequence having sequence homology with the base sequence indicated in SEQ ID NO: 9 of 90% or more and encoding a protein having flavin-binding glucose dehydrogenase enzyme activity.

16. A vector containing the flavin-binding glucose dehydrogenase gene according to claim 15.

17. A host cell containing the vector according to claim 16.

18. A method for producing flavin-binding glucose dehydrogenase gene, comprising the following steps:
culturing the host cell according to claim 17,
expressing a flavin-binding glucose dehydrogenase gene contained in the host cells, and
recovering the flavin-binding glucose dehydrogenase from the culture.

* * * * *

```
                           SEQUENCE LISTING

<160> NUMBER OF SEQ ID NOS: 49

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
                20                  25                  30

Asp Tyr Val Ile Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
        50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
                100                 105                 110

Gly Gly Gly Ser Ala Ile Asn Gly Leu Val Trp Thr Arg Gly Gly Leu
            115                 120                 125

Lys Asp Tyr Asp Ala Trp Glu Glu Leu Gly Asn Pro Gly Trp Asn Gly
        130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
                180                 185                 190

Gln Ser Ala Ser Trp Asn Ala Ser Leu Glu Thr Leu Asp Phe Thr Ala
            195                 200                 205

Leu Pro Asp Ile Leu Asn Gly Thr Leu Ala Gly Tyr Ser Thr Thr Pro
        210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
                260                 265                 270

Leu Lys Ala Thr Gly Val Glu Trp Tyr Pro Thr Gly Asn Lys Asn Gln
```

```
                275                 280                 285
Lys Gln Ile Ile Lys Ala Arg Tyr Glu Val Ile Ile Ser Ser Gly Ala
    290                 295                 300
Ile Gly Ser Pro Lys Leu Leu Glu Ile Ser Gly Ile Gly Asn Lys Asp
305                 310                 315                 320
Ile Val Ser Ala Ala Gly Val Glu Ser Leu Ile Asp Leu Pro Gly Val
                325                 330                 335
Gly Ser Asn Met Gln Asp His Val His Ala Ile Thr Val Ser Thr Thr
            340                 345                 350
Asn Ile Thr Gly Tyr Thr Thr Asn Ser Val Phe Val Asn Glu Thr Leu
        355                 360                 365
Ala Gln Glu Gln Arg Glu Glu Tyr Glu Ala Asn Lys Thr Gly Ile Trp
    370                 375                 380
Ala Thr Thr Pro Asn Asn Leu Gly Tyr Pro Thr Pro Glu Gln Leu Phe
385                 390                 395                 400
Asn Gly Thr Glu Phe Val Ser Gly Lys Glu Phe Ala Asp Lys Ile Arg
                405                 410                 415
Asn Ser Thr Asp Glu Trp Ala Asn Tyr Tyr Ala Ser Thr Asn Ala Ser
            420                 425                 430
Asn Val Glu Leu Leu Lys Lys Gln Tyr Ala Ile Val Ala Ser Arg Tyr
        435                 440                 445
Glu Glu Asn Tyr Leu Ser Pro Ile Glu Ile Asn Phe Thr Pro Gly Tyr
    450                 455                 460
Glu Gly Ser Gly Asn Val Asp Leu Gln Asn Asn Lys Tyr Gln Thr Val
465                 470                 475                 480
Asn His Val Leu Ile Ala Pro Leu Ser Arg Gly Tyr Thr His Ile Asn
                485                 490                 495
Ser Ser Asp Val Glu Asp His Ser Val Ile Asn Pro Gln Tyr Tyr Ser
            500                 505                 510
His Pro Met Asp Ile Asp Val His Ile Ala Ser Thr Lys Leu Ala Arg
        515                 520                 525
Glu Ile Ile Thr Ala Ser Pro Gly Leu Gly Asp Ile Asn Ser Gly Glu
    530                 535                 540
Ile Glu Pro Gly Met Asn Ile Thr Ser Glu Asp Asp Leu Arg Ser Trp
545                 550                 555                 560
Leu Ser Asn Asn Val Arg Ser Asp Trp His Pro Val Gly Thr Cys Ala
                565                 570                 575
Met Leu Pro Lys Glu Leu Gly Gly Val Val Ser Pro Ala Leu Met Val
            580                 585                 590
Tyr Gly Thr Ser Asn Leu Arg Val Val Asp Ala Ser Ile Met Pro Leu
        595                 600                 605
Glu Val Ser Ser His Leu Met Gln Pro Thr Tyr Gly Ile Ala Glu Lys
    610                 615                 620
Ala Ala Asp Ile Ile Lys Asn Phe Tyr Lys Thr Gln His Lys Asn Gln
625                 630                 635                 640
Asn

<210> SEQ ID NO 2
<211> LENGTH: 1926
<212> TYPE: DNA
<213> ORGANISM: Artificial Sequence
<220> FEATURE:
<223> OTHER INFORMATION: GDH gene synthesized by using E.coli codon
      usage
```

<400> SEQUENCE: 2

```
atgaaaatta ccgcggccat tatcaccgtt gcgacggcct ttgcgagctt tgcgtctgcc      60
cagcaggata ccaacagctc tagtaccgat acgtatgatt acgtgattgt tggcggtggc     120
gtggcaggtc tggcactggc aagtcgtatt agcgaaaata aagatgtgac cgttgcagtg     180
ctggaaagcg gtccgaacgc gaatgatcgc tttgtggttt atgccccggg catgtacggt     240
caggcagttg gcaccgatct gtgcccgctg atcccgacca cgccgcagga aaacatgggt     300
aatcgtagcc tgaccattgc aacgggtcgt ctgctgggtg gcggttctgc aatcaacggt     360
ctggtgtgga cccgtggcgg tctgaaagat tatgatgcct gggaagaact gggcaacccg     420
ggttggaacg gcgcaaatct gttcaaatac ttcaaaaaag ttgaaaactt caccccgccg     480
acgccggccc agattgaata tggcgcaacc taccagaaaa gcgcgcatgg taaaaaaggc     540
ccgatcgatg tgtcttttac gaactatgaa tttagccagt ctgcgagttg aatgcctct     600
ctggaaaccc tggatttcac ggcgctgccg gatattctga acggtaccct ggccggctat     660
agcaccacgc cgaatatcct ggatccggaa acggttcagc gtgtggatag ttataccggt     720
tacattgcgc cgtacacgag ccgtaacaat ctgaacgttc tggcaaatca caccgtgtct     780
cgcatccagt ttgcgccgaa aaacggcagt gaaccgctga agccaccgg tgttgaatgg     840
tatccgacgg gcaacaaaaa ccagaaacag atcatcaaag cacgctacga agtgattatc     900
agctctggtc cgattggctc tccgaaactg ctggaaatta gtggcatcgg taataaagat     960
attgttagtg cagcgggtgt ggaaagcctg atcgatctgc cgggcgtggg tagcaacatg    1020
caggatcatg ttcacgcgat taccgtgagt accacgaata tcacgggcta taccacgaac    1080
agcgttttg tgaatgaaac cctggcccag aacagcgtg aagaatatga agcgaacaaa    1140
acgggtattt gggccaccac gccgaacaat ctgggctacc cgaccccgga acagctgttt    1200
aatggtacgg aatttgtgtc tggcaaagaa tttgcggata aaattcgtaa cagtaccgat    1260
gaatgggcaa attattacgc gagcacgaac gcctctaatg ttgaactgct gaaaaaacag    1320
tatgccatcg tggcaagccg ctatgaagaa aactacctgt ctccgattga aatcaatttt    1380
acccccgggtt atgaaggcag cggtaacgtt gatctgcaga acaataaata ccagaccgtt    1440
aatcatgtgc tgattgcgcc gctgagccgt ggctatacgc atatcaacag tagcgatgtt    1500
gaagatcaca gtgtgattaa tccgcagtat tacagccatc cgatggatat tgatgtgcac    1560
atcgcaagca ccaaactggc gcgcgaaatt atcacggcgt ctccgggcct gggtgatatt    1620
aacagtggtg aaatcgaacc gggcatgaat atcaccagtg aagatgatct gcgttcttgg    1680
ctgagtaaca atgttcgcag cgattggcac ccggtgggta cctgtgcgat gctgccgaaa    1740
gaactgggcg gtgtggttag cccggccctg atggtttatg gcaccagcaa cctgcgcgtg    1800
gttgatgcat ctattatgcc gctggaagtg tctagtcatc tgatgcagcc gacctatggc    1860
atcgccgaaa aagccgcaga tatcatcaaa aacttctaca aacccagca caaaaaccag    1920
aattaa                                                              1926
```

<210> SEQ ID NO 3
<211> LENGTH: 36
<212> TYPE: DNA
<213> ORGANISM: Artificial Sequence
<220> FEATURE:
<223> OTHER INFORMATION: primer Mp wild (forward)

<400> SEQUENCE: 3

```
aaggagatat acatatgaaa attaccgcgg ccatta                               36
```

<210> SEQ ID NO 4
<211> LENGTH: 37
<212> TYPE: DNA
<213> ORGANISM: Artificial Sequence
<220> FEATURE:
<223> OTHER INFORMATION: primer Mp (reverse)

<400> SEQUENCE: 4
gctcgaattc ggatccttaa ttctggtttt tgtgctg                              37

<210> SEQ ID NO 5
<211> LENGTH: 34
<212> TYPE: DNA
<213> ORGANISM: Artificial Sequence
<220> FEATURE:
<223> OTHER INFORMATION: primer Mp NS1 (forward)

<400> SEQUENCE: 5
aaggagatat acatatgcag caggatacca acag                                 34

<210> SEQ ID NO 6
<211> LENGTH: 36
<212> TYPE: DNA
<213> ORGANISM: Artificial Sequence
<220> FEATURE:
<223> OTHER INFORMATION: primer Mp NS2 (forward)

<400> SEQUENCE: 6
aaggagatat acatatgcag gataccaaca gctcta                               36

<210> SEQ ID NO 7
<211> LENGTH: 1869
<212> TYPE: DNA
<213> ORGANISM: Artificial Sequence
<220> FEATURE:
<223> OTHER INFORMATION: Synthesized

<400> SEQUENCE: 7
atgcagcagg ataccaacag ctctagtacc gatacgtatg attacgtgat tgttggcggt     60
ggcgtggcag gtctggcact ggcaagtcgt attagcgaaa ataaagatgt gaccgttgca    120
gtgctggaaa gcggtccgaa cgcgaatgat cgctttgtgg tttatgcccc gggcatgtac    180
ggtcaggcag ttggcaccga tctgtgcccg ctgatcccga ccacgccgca ggaaaacatg    240
ggtaatcgta gcctgaccat tgcaacgggt cgtctgctgg gtggcggttc tgcaatcaac    300
ggtctggtgt ggacccgtgg cggtctgaaa gattatgatg cctgggaaga actgggcaac    360
ccgggttgga acggcgcaaa tctgttcaaa tacttcaaaa agttgaaaaa cttcaccccg    420
ccgacgccgg cccagattga atatggcgca acctaccaga aagcgcgcca tggtaaaaaa    480
ggcccgatcg atgtgtcttt tacgaactat gaatttagcc agtctgcgag ttggaatgcc    540
tctctggaaa ccctggattt cacgcgctg ccggatattc tgaacggtac cctgccggc     600 tatagcacca cgccgaatat cctggatccg gaaacggttc agcgtgtgga tagttatacc    660
ggttacattg cgccgtacac gagccgtaac aatctgaacg ttctggcaaa tcacaccgtg    720
tctcgcatcc agtttgcgcc gaaaaacggc agtgaaccgc tgaaagccac cggtgttgaa    780
tggtatccga cgggcaacaa aaaccagaaa cagatcatca agcacgcta cgaagtgatt    840 atcagctctg gtcgcattgg ctctccgaaa ctgctggaaa ttagtggcat cggtaataaa    900
gatattgtta gtgcagcggg tgtggaaagc ctgatcgatc tgccgggcgt gggtagcaac    960

-continued

```
atgcaggatc atgttcacgc gattaccgtg agtaccacga atatcacggg ctataccacg    1020
aacagcgttt ttgtgaatga aaccctggcc caggaacagc gtgaagaata tgaagcgaac    1080
aaaacgggta tttgggccac cacgccgaac aatctgggct acccgacccc ggaacagctg    1140
tttaatggta cggaatttgt gtctggcaaa gaatttgcgg ataaaattcg taacagtacc    1200
gatgaatggg caaattatta cgcgagcacg aacgcctcta atgttgaact gctgaaaaaa    1260
cagtatgcca tcgtggcaag ccgctatgaa gaaaactacc tgtctccgat tgaaatcaat    1320
tttaccccgg gttatgaagg cagcggtaac gttgatctgc agaacaataa ataccagacc    1380
gttaatcatg tgctgattgc gccgctgagc cgtggctata cgcatatcaa cagtagcgat    1440
gttgaagatc acagtgtgat taatccgcag tattacagcc atccgatgga tattgatgtg    1500
cacatcgcaa gcaccaaact ggcgcgcgaa attatcacgg cgtctccggg cctgggtgat    1560
attaacagtg gtgaaatcga accgggcatg aatatcacca gtgaagatga tctgcgttct    1620
tggctgagta acaatgttcg cagcgattgg cacccggtgg gtacctgtgc gatgctgccg    1680
aaagaactgg gcggtgtggt tagcccggcc ctgatggttt atggcaccag caacctgcgc    1740
gtggttgatg catctattat gccgctggaa gtgtctagtc atctgatgca gccgacctat    1800
ggcatcgccg aaaagccgc agatatcatc aaaaacttct acaaacccca gcacaaaaac    1860
cagaattaa                                                             1869
```

<210> SEQ ID NO 8
<211> LENGTH: 622
<212> TYPE: PRT
<213> ORGANISM: Artificial Sequence
<220> FEATURE:
<223> OTHER INFORMATION: Synthesized

<400> SEQUENCE: 8

```
Met Gln Gln Asp Thr Asn Ser Ser Thr Asp Thr Tyr Asp Tyr Val
1               5                   10                  15

Ile Val Gly Gly Val Ala Gly Leu Ala Leu Ala Ser Arg Ile Ser
                20                  25                  30

Glu Asn Lys Asp Val Thr Val Ala Val Leu Glu Ser Gly Pro Asn Ala
            35                  40                  45

Asn Asp Arg Phe Val Val Tyr Ala Pro Gly Met Tyr Gly Gln Ala Val
        50                  55                  60

Gly Thr Asp Leu Cys Pro Leu Ile Pro Thr Thr Pro Gln Glu Asn Met
65                  70                  75                  80

Gly Asn Arg Ser Leu Thr Ile Ala Thr Gly Arg Leu Leu Gly Gly Gly
                85                  90                  95

Ser Ala Ile Asn Gly Leu Val Trp Thr Arg Gly Gly Leu Lys Asp Tyr
            100                 105                 110

Asp Ala Trp Glu Glu Leu Gly Asn Pro Gly Trp Asn Gly Ala Asn Leu
        115                 120                 125

Phe Lys Tyr Phe Lys Lys Val Glu Asn Phe Thr Pro Thr Pro Ala
    130                 135                 140

Gln Ile Glu Tyr Gly Ala Thr Tyr Gln Lys Ser Ala His Gly Lys Lys
145                 150                 155                 160

Gly Pro Ile Asp Val Ser Phe Thr Asn Tyr Glu Phe Ser Gln Ser Ala
                165                 170                 175

Ser Trp Asn Ala Ser Leu Glu Thr Leu Asp Phe Thr Ala Leu Pro Asp
            180                 185                 190

Ile Leu Asn Gly Thr Leu Ala Gly Tyr Ser Thr Thr Pro Asn Ile Leu
```

```
                195                 200                 205
Asp Pro Glu Thr Val Gln Arg Val Asp Ser Tyr Thr Gly Tyr Ile Ala
210                 215                 220

Pro Tyr Thr Ser Arg Asn Asn Leu Asn Val Leu Ala Asn His Thr Val
225                 230                 235                 240

Ser Arg Ile Gln Phe Ala Pro Lys Asn Gly Ser Glu Pro Leu Lys Ala
                245                 250                 255

Thr Gly Val Glu Trp Tyr Pro Thr Gly Asn Lys Asn Gln Lys Gln Ile
            260                 265                 270

Ile Lys Ala Arg Tyr Glu Val Ile Ser Ser Gly Ala Ile Gly Ser
        275                 280                 285

Pro Lys Leu Leu Glu Ile Ser Gly Ile Gly Asn Lys Asp Ile Val Ser
        290                 295                 300

Ala Ala Gly Val Glu Ser Leu Ile Asp Leu Pro Gly Val Gly Ser Asn
305                 310                 315                 320

Met Gln Asp His Val His Ala Ile Thr Val Ser Thr Thr Asn Ile Thr
                325                 330                 335

Gly Tyr Thr Thr Asn Ser Val Phe Val Asn Glu Thr Leu Ala Gln Glu
            340                 345                 350

Gln Arg Glu Glu Tyr Glu Ala Asn Lys Thr Gly Ile Trp Ala Thr Thr
        355                 360                 365

Pro Asn Asn Leu Gly Tyr Pro Thr Pro Glu Gln Leu Phe Asn Gly Thr
370                 375                 380

Glu Phe Val Ser Gly Lys Glu Phe Ala Asp Lys Ile Arg Asn Ser Thr
385                 390                 395                 400

Asp Glu Trp Ala Asn Tyr Tyr Ala Ser Thr Asn Ala Ser Asn Val Glu
                405                 410                 415

Leu Leu Lys Lys Gln Tyr Ala Ile Val Ala Ser Arg Tyr Glu Glu Asn
            420                 425                 430

Tyr Leu Ser Pro Ile Glu Ile Asn Phe Thr Pro Gly Tyr Glu Gly Ser
        435                 440                 445

Gly Asn Val Asp Leu Gln Asn Asn Lys Tyr Gln Thr Val Asn His Val
        450                 455                 460

Leu Ile Ala Pro Leu Ser Arg Gly Tyr Thr His Ile Asn Ser Ser Asp
465                 470                 475                 480

Val Glu Asp His Ser Val Ile Asn Pro Gln Tyr Tyr Ser His Pro Met
                485                 490                 495

Asp Ile Asp Val His Ile Ala Ser Thr Lys Leu Ala Arg Glu Ile Ile
            500                 505                 510

Thr Ala Ser Pro Gly Leu Gly Asp Ile Asn Ser Gly Glu Ile Glu Pro
        515                 520                 525

Gly Met Asn Ile Thr Ser Glu Asp Leu Arg Ser Trp Leu Ser Asn
        530                 535                 540

Asn Val Arg Ser Asp Trp His Pro Val Gly Thr Cys Ala Met Leu Pro
545                 550                 555                 560

Lys Glu Leu Gly Gly Val Val Ser Pro Ala Leu Met Val Tyr Gly Thr
                565                 570                 575

Ser Asn Leu Arg Val Val Asp Ala Ser Ile Met Pro Leu Glu Val Ser
            580                 585                 590

Ser His Leu Met Gln Pro Thr Tyr Gly Ile Ala Glu Lys Ala Ala Asp
        595                 600                 605

Ile Ile Lys Asn Phe Tyr Lys Thr Gln His Lys Asn Gln Asn
        610                 615                 620
```

<210> SEQ ID NO 9
<211> LENGTH: 1866
<212> TYPE: DNA
<213> ORGANISM: Artificial Sequence
<220> FEATURE:
<223> OTHER INFORMATION: Synthesized

<400> SEQUENCE: 9

```
atgcaggata ccaacagctc tagtaccgat acgtatgatt acgtgattgt tggcggtggc      60
gtggcaggtc tggcactggc aagtcgtatt agcgaaaata aagatgtgac cgttgcagtg     120
ctggaaagcg gtccgaacgc gaatgatcgc tttgtggttt atgccccggg catgtacggt     180
caggcagttg gcaccgatct gtgcccgctg atcccgacca cgccgcagga aaacatgggt     240
aatcgtagcc tgaccattgc aacgggtcgt ctgctgggtg gcggttctgc aatcaacggt     300
ctggtgtgga cccgtggcgg tctgaaagat tatgatgcct gggaagaact gggcaacccg     360
ggttggaacg cgcaaatctg ttcaaatac ttcaaaaaag ttgaaaactt cacccccgccg     420
acgccggccc agattgaata tggcgcaacc taccagaaaa gcgcgcatgg taaaaaaggc     480
ccgatcgatg tgtcttttac gaactatgaa tttagccagt ctgcgagttg aatgcctct     540
ctggaaaccc tggatttcac ggcgctgccg atattctga acggtaccct ggccggctat     600
agcaccacgc cgaatatcct ggatccggaa acgttcagc gtgtggatag ttataccggt     660
tacattgcgc cgtacacgag ccgtaacaat ctgaacgttc tggcaaatca caccgtgtct     720
cgcatccagt ttgcgccgaa aaacggcagt gaaccgctga agccaccgg tgttgaatgg     780
tatccgacgg gcaacaaaaa ccagaaacag atcatcaaag cacgctacga agtgattatc     840
agctctggtg cgattggctc tccgaaactg ctggaaatta gtggcatcgg taataaagat     900
attgttagtg cagcgggtgt ggaaagcctg atcgatctgc cgggcgtggg tagcaacatg     960
caggatcatg ttcacgcgat taccgtgagt accacgaata tcacgggcta taccacgaac    1020
agcgtttttg tgaatgaaac cctggcccag gaacagcgtg aagaatatga gcgaacaaa    1080
acgggtattt gggccaccac gccgaacaat ctgggctacc cgaccccgga acagctgttt    1140
aatggtacgg aatttgtgtc tggcaaagaa tttgcggata aaattcgtaa cagtaccgat    1200
gaatgggcaa attattacgc gagcacgaac gcctctaatg ttgaactgct gaaaaaacag    1260
tatgccatcg tggcaagccg ctatgaagaa aactacctgt ctccgattga atcaattttt    1320
accccgggtt atgaaggcag cggtaacgtt gatctgcaga caataaata ccagaccgtt    1380
aatcatgtgc tgattgcgcc gctgagccgt ggctatacgc atatcaacag tagcgatgtt    1440
gaagatcaca gtgtgattaa tccgcagtat tacagccatc cgatggatat tgatgtgcac    1500
atcgcaagca ccaaactggc gcgcgaaatt atcacgcgt ctccgggcct gggtgatatt    1560
aacagtggtg aaatcgaacc gggcatgaat atcaccagtg aagatgatct cgttcttgg    1620
ctgagtaaca atgttcgcag cgattggcac ccggtgggta cctgtgcgat gctgccgaaa    1680
gaactgggcg gtgtggttag cccggccctg atggtttatg gcaccagcaa cctgcgcgtg    1740
gttgatgcat ctattatgcc gctggaagtg tctagtcatc tgatgcagcc gacctatggc    1800
atcgccgaaa aagccgcaga tatcatcaaa aacttctaca aacccagca caaaaccag    1860
aattaa                                                              1866
```

<210> SEQ ID NO 10
<211> LENGTH: 621
<212> TYPE: PRT

<213> ORGANISM: Artificial Sequence
<220> FEATURE:
<223> OTHER INFORMATION: Synthesized

<400> SEQUENCE: 10

```
Met Gln Asp Thr Asn Ser Ser Thr Asp Thr Tyr Asp Tyr Val Ile
1               5                   10                  15

Val Gly Gly Gly Val Ala Gly Leu Ala Leu Ala Ser Arg Ile Ser Glu
            20                  25                  30

Asn Lys Asp Val Thr Val Ala Leu Glu Ser Gly Pro Asn Ala Asn
        35                  40                  45

Asp Arg Phe Val Val Tyr Ala Pro Gly Met Tyr Gly Gln Ala Val Gly
        50                  55                  60

Thr Asp Leu Cys Pro Leu Ile Pro Thr Thr Pro Gln Glu Asn Met Gly
65                  70                  75                  80

Asn Arg Ser Leu Thr Ile Ala Thr Gly Arg Leu Leu Gly Gly Gly Ser
                85                  90                  95

Ala Ile Asn Gly Leu Val Trp Thr Arg Gly Gly Leu Lys Asp Tyr Asp
                100                 105                 110

Ala Trp Glu Glu Leu Gly Asn Pro Gly Trp Asn Gly Ala Asn Leu Phe
            115                 120                 125

Lys Tyr Phe Lys Lys Val Glu Asn Phe Thr Pro Pro Thr Pro Ala Gln
130                 135                 140

Ile Glu Tyr Gly Ala Thr Tyr Gln Lys Ser Ala His Gly Lys Lys Gly
145                 150                 155                 160

Pro Ile Asp Val Ser Phe Thr Asn Tyr Glu Phe Ser Gln Ser Ala Ser
                165                 170                 175

Trp Asn Ala Ser Leu Glu Thr Leu Asp Phe Thr Ala Leu Pro Asp Ile
                180                 185                 190

Leu Asn Gly Thr Leu Ala Gly Tyr Ser Thr Thr Pro Asn Ile Leu Asp
            195                 200                 205

Pro Glu Thr Val Gln Arg Val Asp Ser Tyr Thr Gly Tyr Ile Ala Pro
    210                 215                 220

Tyr Thr Ser Arg Asn Asn Leu Asn Val Leu Ala Asn His Thr Val Ser
225                 230                 235                 240

Arg Ile Gln Phe Ala Pro Lys Asn Gly Ser Glu Pro Leu Lys Ala Thr
                245                 250                 255

Gly Val Glu Trp Tyr Pro Thr Gly Asn Lys Asn Gln Lys Gln Ile Ile
            260                 265                 270

Lys Ala Arg Tyr Glu Val Ile Ile Ser Ser Gly Ala Ile Gly Ser Pro
        275                 280                 285

Lys Leu Leu Glu Ile Ser Gly Ile Gly Asn Lys Asp Ile Val Ser Ala
    290                 295                 300

Ala Gly Val Glu Ser Leu Ile Asp Leu Pro Gly Val Gly Ser Asn Met
305                 310                 315                 320

Gln Asp His Val His Ala Ile Thr Val Ser Thr Thr Asn Ile Thr Gly
                325                 330                 335

Tyr Thr Thr Asn Ser Val Phe Val Asn Glu Thr Leu Ala Gln Glu Gln
            340                 345                 350

Arg Glu Glu Tyr Glu Ala Asn Lys Thr Gly Ile Trp Ala Thr Thr Pro
        355                 360                 365

Asn Asn Leu Gly Tyr Pro Thr Pro Glu Gln Leu Phe Asn Gly Thr Glu
    370                 375                 380

Phe Val Ser Gly Lys Glu Phe Ala Asp Lys Ile Arg Asn Ser Thr Asp
```

```
                385                 390                 395                 400
        Glu Trp Ala Asn Tyr Tyr Ala Ser Thr Asn Ala Ser Asn Val Glu Leu
                        405                 410                 415

Leu Lys Lys Gln Tyr Ala Ile Val Ala Ser Arg Tyr Glu Glu Asn Tyr
                        420                 425                 430

Leu Ser Pro Ile Glu Ile Asn Phe Thr Pro Gly Tyr Glu Gly Ser Gly
                        435                 440                 445

Asn Val Asp Leu Gln Asn Asn Lys Tyr Gln Thr Val Asn His Val Leu
                        450                 455                 460

Ile Ala Pro Leu Ser Arg Gly Tyr Thr His Ile Asn Ser Ser Asp Val
        465                 470                 475                 480

Glu Asp His Ser Val Ile Asn Pro Gln Tyr Tyr Ser His Pro Met Asp
                        485                 490                 495

Ile Asp Val His Ile Ala Ser Thr Lys Leu Ala Arg Glu Ile Ile Thr
                        500                 505                 510

Ala Ser Pro Gly Leu Gly Asp Ile Asn Ser Gly Glu Ile Glu Pro Gly
                        515                 520                 525

Met Asn Ile Thr Ser Glu Asp Asp Leu Arg Ser Trp Leu Ser Asn Asn
                        530                 535                 540

Val Arg Ser Asp Trp His Pro Val Gly Thr Cys Ala Met Leu Pro Lys
        545                 550                 555                 560

Glu Leu Gly Gly Val Val Ser Pro Ala Leu Met Val Tyr Gly Thr Ser
                        565                 570                 575

Asn Leu Arg Val Val Asp Ala Ser Ile Met Pro Leu Glu Val Ser Ser
                        580                 585                 590

His Leu Met Gln Pro Thr Tyr Gly Ile Ala Glu Lys Ala Ala Asp Ile
                        595                 600                 605

Ile Lys Asn Phe Tyr Lys Thr Gln His Lys Asn Gln Asn
                        610                 615                 620

<210> SEQ ID NO 11
<211> LENGTH: 30
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (15)..(17)
<223> OTHER INFORMATION: n is a, c, g, or t

<400> SEQUENCE: 11
tggatccgga aacgnnncag cgtgtggata                                     30

<210> SEQ ID NO 12
<211> LENGTH: 30
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (14)..(16)
<223> OTHER INFORMATION: n is a, c, g, or t

<400> SEQUENCE: 12
tatccacacg ctgnnncgtt tccggatcca                                     30

<210> SEQ ID NO 13
<211> LENGTH: 30
```

```
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (7)..(9)
<223> OTHER INFORMATION: n is a, c, g, or t

<400> SEQUENCE: 13
gccaccnnnc cgaacaatct gggctacccg                                    30

<210> SEQ ID NO 14
<211> LENGTH: 28
<212> TYPE: DNA
<213> ORGANISM: Artificial Sequence
<220> FEATURE:
<223> OTHER INFORMATION: Sythesized Oligonucleotide
<220> FEATURE:
<221> NAME/KEY: misc_feature
<222> LOCATION: (4)..(6)
<223> OTHER INFORMATION: n is a, c, g, or t

<400> SEQUENCE: 14
cggnnnggtg gcccaaatac ccgttttg                                      28

<210> SEQ ID NO 15
<211> LENGTH: 30
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (9)..(11)
<223> OTHER INFORMATION: n is a, c, g, or t

<400> SEQUENCE: 15
gtggtgaann ngaaccgggc atgaatatca                                    30

<210> SEQ ID NO 16
<211> LENGTH: 30
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (8)..(10)
<223> OTHER INFORMATION: n is a, c, g, or t

<400> SEQUENCE: 16
ccggttcnnn ttcaccactg ttaatatcac                                    30

<210> SEQ ID NO 17
<211> LENGTH: 26
<212> TYPE: DNA
<213> ORGANISM: Artificial Sequence
<220> FEATURE:
<223> OTHER INFORMATION: primer T368A (forward)

<400> SEQUENCE: 17
ccaccgcgcc gaacaatctg ggctac                                        26

<210> SEQ ID NO 18
<211> LENGTH: 26
<212> TYPE: DNA
<213> ORGANISM: Artificial Sequence
<220> FEATURE:
```

<223> OTHER INFORMATION: primer T368A (reverse)

<400> SEQUENCE: 18
gcgcggtggc ccaaataccc gttttg        26

<210> SEQ ID NO 19
<211> LENGTH: 20
<212> TYPE: PRT
<213> ORGANISM: Mucor prainii

<400> SEQUENCE: 19

Met Lys Ile Thr Ala Ala Ile Ile Thr Val Ala Thr Ala Phe Ala Ser
1               5                   10                  15

Phe Ala Ser Ala
            20

<210> SEQ ID NO 20
<211> LENGTH: 21
<212> TYPE: PRT
<213> ORGANISM: Mucor prainii

<400> SEQUENCE: 20

Met Lys Ile Thr Ala Ala Ile Ile Thr Val Ala Thr Ala Phe Ala Ser
1               5                   10                  15

Phe Ala Ser Ala Gln
            20

<210> SEQ ID NO 21
<211> LENGTH: 27
<212> TYPE: PRT
<213> ORGANISM: Mucor prainii

<400> SEQUENCE: 21

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser
            20                  25

<210> SEQ ID NO 22
<211> LENGTH: 28
<212> TYPE: PRT
<213> ORGANISM: Mucor prainii

<400> SEQUENCE: 22

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser
            20                  25

<210> SEQ ID NO 23
<211> LENGTH: 1926
<212> TYPE: DNA
<213> ORGANISM: Mucor prainii

<400> SEQUENCE: 23
atgaagatca cagctgccat tatcactgtt gccacagcat ttgcttcttt tgcttctgct        60
caacaagaca caaattcttc ctcaactgat acttatgatt atgttatcgt tggcggcggt       120
gtagctggtt tggcttttgg tagtcgtatc tctgaaaaca aggatgtcac tgttgctgtt       180
ctcgagtccg gtcctaatgc caatgataga tttgttgttt atgctcctgg catgtatggc       240
caagctgttg gcactgatct ctgtcctctc attcctacta ctcctcaaga aaatatgggc       300

```
aacagaagtc tcacaatcgc tactggtaga ttgctcggtg gtggcagtgc tattaatggt    360
ctcgtttgga cccgtggtgg cttgaaggat tacgatgctt gggaggagct cggtaaccct    420
ggatggaacg gtgccaactt gttcaagtac tttaagaagg tcgaaaactt cactcctcct    480
actcctgccc aaattgaata cggcgctact tatcagaaaa gtgctcatgg caagaaggga    540
cctattgatg tctctttcac gaactacgag ttctctcaat ctgctagctg aacgcctca    600 ctcgaaaccc ttgatttcac tgcacttcct gatatcttga acggtacttt ggccggttac    660
tctaccactc ccaacatttt ggaccctgag actgttcaac gtgttgattc ctatactggt    720
tacattgctc cttacactag ccgtaacaac ctcaatgttt tggccaacca taccgtctcc    780
cgcattcaat ttgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctactac tcccaacaac ctcggttatc ctacgcccga caactcttc    1200 aatggcaccg aattcgtttc tggaaaggag tttgctgaca agattcgtaa ctctactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgagggtag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc ctatggatat tgatgtccat   1560
atcgcttcca ctaaacttgc tcgcgaaatc atcactgcct ctcccggtct tggtgacatt   1620
aacagtggcg aaatcgaacc cggtatgaat attacttctg aagacgacct tagatcttgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                               1926
```

<210> SEQ ID NO 24
<211> LENGTH: 45
<212> TYPE: DNA
<213> ORGANISM: Artificial Sequence
<220> FEATURE:
<223> OTHER INFORMATION: Artificially Synthesized Primer Sequence

<400> SEQUENCE: 24
ggaatattaa gcttggtacc atgaagatca cagctgccat tatca    45

<210> SEQ ID NO 25
<211> LENGTH: 48
<212> TYPE: DNA
<213> ORGANISM: Artificial Sequence
<220> FEATURE:
<223> OTHER INFORMATION: Artificially Synthesized Primer Sequence

<400> SEQUENCE: 25
gtggatccga gctcggtacc ctaattttgg ttcttgtgtt gagtcttg            48

<210> SEQ ID NO 26
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 26
gaccctgaga ctgctcaacg tgttgattcc            30

<210> SEQ ID NO 27
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 27
aatgtaacca gtataggaat caacacgttg            30

<210> SEQ ID NO 28
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 28
gaccctgaga cttgtcaacg tgttgattcc            30

<210> SEQ ID NO 29
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 29
gaccctgaga ctatgcaacg tgttgattcc            30

<210> SEQ ID NO 30
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 30
gaccctgaga ctcaacaacg tgttgattcc            30

<210> SEQ ID NO 31
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 31
gaccctgaga ctgagcaacg tgttgattcc            30

<210> SEQ ID NO 32
<211> LENGTH: 30
<212> TYPE: DNA
<213> ORGANISM: Artificial Sequence

```
<220> FEATURE:
<223> OTHER INFORMATION: Artificially Synthesized Primer Sequence

<400> SEQUENCE: 32
atctgggcta ctgctcccaa caacctcggt                                              30

<210> SEQ ID NO 33
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 33
ttcgggcgta ggataaccga ggttgttggg                                              30

<210> SEQ ID NO 34
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 34
atctgggcta cttgtcccaa caacctcggt                                              30

<210> SEQ ID NO 35
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 35
atctgggcta ctagtcccaa caacctcggt                                              30

<210> SEQ ID NO 36
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 36
atctgggcta ctggtcccaa caacctcggt                                              30

<210> SEQ ID NO 37
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 37
aacagtggcg aaaccgaacc cggtatgaat                                              30

<210> SEQ ID NO 38
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 38
gtcttcagaa gtaatattca taccgggttc                                              30
```

```
<210> SEQ ID NO 39
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 39
aacagtggcg aaagcgaacc cggtatgaat                                    30

<210> SEQ ID NO 40
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 40
aacagtggcg aacccgaacc cggtatgaat                                    30

<210> SEQ ID NO 41
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 41
gctattaatg gtatggtttg gacccgtggt                                    30

<210> SEQ ID NO 42
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 42
gtaatccttc aagccaccac gggtccaaac                                    30

<210> SEQ ID NO 43
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 43
gtccgttctg actatcatcc tgttggtact                                    30

<210> SEQ ID NO 44
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 44
gggaagcata gcacaagtac caacaggatg                                    30

<210> SEQ ID NO 45
<211> LENGTH: 30
<212> TYPE: DNA
<213> ORGANISM: Artificial Sequence
<220> FEATURE:
<223> OTHER INFORMATION: Artificially Synthesized Primer Sequence
```

```
<400> SEQUENCE: 45
ctcgaagtct cttgtcattt gatgcaaccc                                    30

<210> SEQ ID NO 46
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 46
gcaataccgt aggtgggttg catcaaatg                                     29

<210> SEQ ID NO 47
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 47
ctcgaagtct ctactcattt gatgcaaccc                                    30

<210> SEQ ID NO 48
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 48
gaaccgggca tgaatatcac cagtgaagat                                    30

<210> SEQ ID NO 49
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 49
attcatgccc ggttcagttt caccactgtt                                    30
```